US010154955B2

(12) United States Patent
Rana et al.

(10) Patent No.: US 10,154,955 B2
(45) Date of Patent: Dec. 18, 2018

(54) **COMPOSITIONS INCLUDING *BAUHINIA*, METHODS OF MAKING AND USING THE SAME IN SKIN ANTI-AGING AND OTHER SKIN APPLICATIONS**

(71) Applicant: ACCESS BUSINESS GROUP INTERNATIONAL LLC, Ada, MI (US)

(72) Inventors: Jatinder Rana, Grand Rapids, MI (US); Arun Rajgopal, Grand Rapids, MI (US); Louise M. Schneider, Rockford, MI (US); Jeffrey Scholten, West Olive, MI (US); Yi Zhang, Shanghai (CN); Stephen R. Missler, Grand Rapids, MI (US); Timothy Mulder, Allendale, MI (US)

(73) Assignee: ACCESS BUSINESS GROUP INTERNATIONAL LLC, Ada, MI (US)

( * ) Notice: Subject to any disclaimer, the term of this patent is extended or adjusted under 35 U.S.C. 154(b) by 20 days.

(21) Appl. No.: 15/605,557

(22) Filed: May 25, 2017

(65) Prior Publication Data

US 2018/0000723 A1    Jan. 4, 2018

Related U.S. Application Data

(60) Provisional application No. 62/357,611, filed on Jul. 1, 2016.

(51) Int. Cl.
*A61K 8/9789*    (2017.01)
*A61K 36/48*     (2006.01)
(Continued)

(52) U.S. Cl.
CPC .......... *A61K 8/9789* (2017.08); *A61K 8/0208* (2013.01); *A61K 8/365* (2013.01); *A61K 8/368* (2013.01); *A61K 8/4973* (2013.01); *A61K 8/66* (2013.01); *A61K 36/48* (2013.01); *A61Q 19/02* (2013.01); *A61Q 19/08* (2013.01); *A61K 2800/78* (2013.01)

(58) Field of Classification Search
CPC .... A61K 8/9789; A61K 36/48; A61K 8/0208; A61K 8/365; A61K 8/368; A61K 8/66; A61K 8/4973; A61K 2800/78; A61Q 19/08; A61Q 19/02
See application file for complete search history.

(56) References Cited

U.S. PATENT DOCUMENTS 5,296,231 A    3/1994  Yarosh
6,096,334 A    8/2000  Rolf et al.
(Continued)

FOREIGN PATENT DOCUMENTS

WO    WO 2018/004901 A1    1/2018

OTHER PUBLICATIONS

Murga, et al., "Extraction of Natural Complex Phenols and Tannins from Grape Seeds by Using Supercritical Mixtures of Carbon Dioxide and Alcohol," *J. Agric Food Chem*, 48(8):3408-3412 (2000).
(Continued)

*Primary Examiner* — Trevor Love
(74) *Attorney, Agent, or Firm* — Brinks Gilson & Lione

(57) ABSTRACT

Topical compositions, packaging systems and methods for improving the appearance of skin or at least one sign of aging in skin including Kachnar are described.

11 Claims, 6 Drawing Sheets

(51) Int. Cl.
   *A61Q 19/08* (2006.01)
   *A61Q 19/02* (2006.01)
   *A61K 8/02* (2006.01)
   *A61K 8/365* (2006.01)
   *A61K 8/368* (2006.01)
   *A61K 8/66* (2006.01)
   *A61K 8/49* (2006.01)

(56) References Cited

U.S. PATENT DOCUMENTS

| | | |
|---|---|---|
| 6,120,792 A | 9/2000 | Juni |
| 6,368,594 B1 | 4/2002 | Doetsch et al. |
| 6,495,158 B1 | 12/2002 | Buseman et al. |
| 6,623,751 B2 | 9/2003 | Gueret |
| 8,697,099 B2 | 4/2014 | Scimeca et al. |
| 2002/0086043 A1 | 7/2002 | Gueret |
| 2002/0183248 A1 | 12/2002 | Oldham et al. |
| 2003/0152610 A1 | 8/2003 | Rolf et al. |
| 2003/0175328 A1 | 9/2003 | Shefer et al. |
| 2005/0019426 A1 | 1/2005 | Wirth et al. |
| 2005/0084547 A1 | 4/2005 | Subbiah |
| 2006/0257386 A1 | 11/2006 | Zimmerman et al. |
| 2009/0247477 A1 | 10/2009 | Talalay et al. |
| 2014/0099273 A1 | 4/2014 | Florence et al. |
| 2014/0155961 A1 | 6/2014 | Morariu |

OTHER PUBLICATIONS

Hong, et al., "Microwave-Assisted Extraction of Phenolic Compounds from Grape Seed," *Natural Product Letters*, 15(3):197-204 (2001).

Ashraf-Khorassani et al., "Sequential Fractionation of Grape Seeds into Oils, Polyphenols, and Procyanidins via a Single System Employing $CO_2$-Based Fluids," *J. Agric Food Chem.*, 52(9):2440-2444 (2004).

CTFA Cosmetic Ingredient Handbook, *The Cosmetic, Toiletry and Fragrance Association*, pp. 272-273 (1992).

Notification of Transmittal and International Search Report and Written Opinion received in PCT Application No. PCT/US2017/34530 dated Aug. 23, 2017.

Master regulator of Total Antioxidant

COMPOSITIONS INCLUDING *BAUHINIA*, METHODS OF MAKING AND USING THE SAME IN SKIN ANTI-AGING AND OTHER SKIN APPLICATIONS

RELATED APPLICATIONS

The present patent document claims the benefit of the filing date under 35 U.S.C. § 119(e) of Provisional U.S. Patent Application Ser. No. 62/357,611, filed Jul. 1, 2016, which is hereby incorporated by reference.

BACKGROUND

Topical compositions that include *Bauhinia*, individually or in combination with at least one other botanical extract and methods of use of the compositions to provide skin anti-aging and other skin effects are described. The disclosed compositions and methods may prevent, reduce, or reverse signs of premature aging, and/or improve the aesthetic appearance of skin. Use of the compositions may stimulate the skin's natural ability to recover from environmental stresses and prevent signs of premature aging as well as lighten the skin. The compositions include natural active ingredients derived from natural plant materials, as well as enzymes for repairing DNA damage and excipients and carriers.

The skin is made up of two major layers. The stratum corneum, or epidermis, is the top or outer layer of the skin. The primary function of the stratum corneum is to provide a protective covering and retard evaporative water loss from the aqueous interior. This is commonly referred to as the barrier function. The stratum corneum protects against mechanical insults, the ingress of foreign chemicals and assaults by microorganisms. It also provides the first defense against ultraviolet light, screening out more than 80% of incident ultraviolet B irradiation.

The dermis lies under the epidermis and makes up 90 percent of the skin's thickness. The dermis contains a dense meshwork of collagen and elastin, providing strength and elasticity to the skin. Fibroblasts constitute the main cell type present in the dermis. Fibroblasts are responsible for synthesis and secretion of dermal matrix components, including collagen, elastin, and glycosaminoglycans (such as hyaluronic acid). Whereas collagen provides strength to the skin and elastin its elasticity, glycosaminoglycans serve to keep the skin moist and plump.

To stay healthy, the skin must cope with changing environmental conditions, while simultaneously repairing damage. Environmental factors play a chief role in aging, wrinkles, skin discolorations and degenerative skin conditions. Exposure to sunlight and UV radiation are major factors resulting in skin damage, accounting for 90% of the symptoms of premature aging. Importantly, exposure to oxygen, sunlight, and other environmental or lifestyle stresses induces the formation of free-radicals. Free radicals can cause wrinkles by activating metalloproteases, such as collagenases, that are responsible for breaking down the skin's connective tissues (collagen and elastin). The result is premature aging. Free-radical damage can also cause a reduction in the thickness of the dermal layer. This can cause the skin to slacken. The slackening of the skin is the first and most visible sign of aging and a cause of wrinkles and lines.

Sunlight also can cause the accumulation of abnormal elastin by triggering the overproduction of metalloproteinases. Normally, metalloproteinases remodel sun-injured skin by manufacturing and reforming collagen. Repeatedly subjecting the skin to this imperfect rebuilding process may lead to formation of wrinkles or solar scars. Exposure to the sun also can rob the skin of essential moisture and create a stressed barrier that does not function properly. As moisture loss and irritation increase, the skin becomes sensitive, scaly, and dry.

Although oxygen and sunlight constitute the principal sources of free-radical damage, other contributors include cigarette smoke, environmental toxins, herbicides, pesticides, weather, diet, stress, sleep deprivation, excessive alcohol consumption, and pollution.

UV radiation from the sun may also damage DNA and may bring about several detrimental effects including cell death, mutation and neoplastic transformation. Studies indicate that some of these deleterious effects are due to the formation of two major classes of bipyrimidine DNA photoproducts, cyclobutane pyrimidine dimers (CPDs) and (6-4) photoproducts (6-4 PPs). Organisms have evolved several different pathways for removing CPDs and 6-4 PPs from cellular DNA. These pathways include various excision repair pathways which can be highly specific or non-specific for CPDs and 6-4 PPs.

In view of the many detrimental effects impacting the skin, there is a demand for cosmetic compositions and cosmetic methods for improving the appearance and condition of skin. Consumers seek "anti-aging" cosmetic products that treat or delay the visible signs of actual aging and weathered skin, such as wrinkles, lines, sagging, hyperpigmentation and age spots. Consumers also seek other benefits from cosmetic products in addition to anti-aging benefits. For example, the concept of "sensitive skin" has raised the demand for cosmetic products that improve the appearance and condition of sensitive, dry and/or flaky skin, and that soothe red, and/or irritated skin. Consumers also desire cosmetic products that treat spots, pimples, blemishes, and the like, or that reduce the risk of skin cancer.

In spite of the various anti-aging cosmetic products on the market for the treatment of skin, there remains a need for effective topically applied cosmetic compositions that provide anti-aging or rejuvenating benefits to the skin, hair and/or nails using natural ingredients as active components. Unnatural, chemically-synthesized products may be perceived as being environmentally or personally unsafe. In contrast, natural products are perceived as pure, mild, and superior to chemically synthesized products.

Natural based products extracted from plants or herbs are believed to contain antioxidant/free-radical scavenging agents that can neutralize the effects of free-radical damage. Additionally, natural-based products can contain agents that stimulate the synthesis and restoration of damaged connective tissue structures in the dermis and barrier function in the epidermis.

However, delivering a cosmetic benefit from "natural" sources, such as plants or herbs, is not trivial. Deriving a real benefit from such sources requires identification of specific plant/herbal extracts or ingredients, their minimum active concentrations, and their additive or synergistic activities in combination with other ingredients to impart anti-aging and/or skin improvement benefits.

The present compositions further address the frequent irritation problems associated with exfoliating agents such as retinoids (e.g., tretinoin, retinol and retinal), carboxylic acids including α-hydroxy acids (e.g., lactic acid, glycolic acid), β-hydroxy acids (e.g., salicylic acid), α-keto acids, acetic acid and trichloroacetic acid, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, benzoyl peroxide and phenol, among others. Exfoliants and other ingredients may also increase the skin's sensitivity to environmental conditions such as sunlight, wind, cold temperature and dry air, or may exacerbate the irritation attributable to a pre-existing skin disease.

Provided are cosmetic compositions for topical use that have anti-aging, anti-oxidant, anti-irritant, anti-inflammatory, and/or aesthetic improvement properties.

SUMMARY

One embodiment relates to a topical composition that includes an amount of a plant ingredient and/or plant extract of *Bauhinia* (also referred to as Kachnar) effective to improve the appearance of skin or at least one sign of aging in skin; and at least one pharmaceutically or cosmetically acceptable vehicle. In certain embodiments, the topical composition may further include at least one other plant ingredient and/or a plant extract, such as a plant extract and/or plant ingredient of *Sesamum* (also referred to as Sesamin). The topical composition may further comprise at least one DNA repair enzyme. The at least one DNA repair enzyme may be a pyrimidine glycosylate/abasic lyase. The at least one DNA repair enzyme may be selected from the group consisting of a bacteriophage T4 pyrimidine dimer-specific endonuclease, a *Micrococcus luteus* N-glycosylase/AP lyase, a *Saccharomyces cerevisiae* N-glycosylase/apurinic-apyrimidinic lyase, a *Schizosaccharomyces pombe* UV damage endonuclease (UVDE), a *Chlorella* virus isolate PBCV-1 pyrimidine dimer-specific glycosylase, an *Anacystis nidulans* photolyase, and combinations thereof. The composition may be in a product form selected from the group consisting of an aerosol, a cream, a emulsion, a solid, a liquid, a dispersion, a foam, a gel, a lotion, a mousse, an ointment, a powder, a patch, a pomade, a solution, a pump a spray, a stick, a towelette, and combinations thereof. The at least one pharmaceutically or cosmetically acceptable vehicle may include one or more ingredients selected from the group consisting of water, a glycerin, a C1-C4 alcohol, a fatty alcohol, a fatty ether, a fatty ester, a polyol, a glycol, a vegetable oil, a mineral oil, a liposome, a laminar lipid material, a silicone oil, and combinations thereof. The composition may have a substantially neutral pH. The topical composition may further include a skin whitening agent selected from the group consisting of tyrosinase inhibitors, free radical scavengers, and mixtures thereof. In the topical composition the amount of a plant ingredient and/or plant extract of *Bauhinia*, individually or in combination with at least one plant ingredient or plant extract from *Sesamum*, effective to improve the appearance of skin or at least one sign of aging in skin can range from about 0.0001% to 5% by weight of the total composition. Alternatively, in the topical composition, the amount of a plant ingredient and/or plant extract of *Bauhinia*, individually or in combination with a plant ingredient or plant extract of *Sesamum*, effective to improve the appearance of skin or at least one sign of aging in skin can range from about 0.001% to about 0.5% by weight of the total composition. Alternatively, in the topical composition the amount of a plant ingredient and/or plant extract of *Bauhinia*, individually or in combination with the amount of a plant ingredient or plant extract of *Sesamum*, effective to improve the appearance of skin or at least one sign of aging in skin can range from about 0.01% to about 0.1% by weight of the total composition.

Another embodiment relates to a packaging system for improving the appearance of skin or at least one sign of aging in skin that includes one or more containers collectively containing the composition that includes an amount of a plant ingredient and/or plant extract of *Bauhinia* effective to improve the appearance of skin or at least one sign of aging in skin and at least one pharmaceutically or cosmetically acceptable vehicle, and instructions for applying the composition from said one or more containers. In certain embodiments, the composition may further include at least one other plant ingredient and/or a plant extract, such as a plant extract and/or plant ingredient of *Sesamum*.

A further embodiment relates to a method of improving the appearance of skin or at least one sign of aging in the skin, the method comprising topically applying to the skin a composition in a cosmetically effective amount sufficient to improve the appearance of the skin or the at least one sign of aging in skin, wherein the composition comprises an amount of a plant ingredient and/or plant extract of *Bauhinia* effective to improve the appearance of skin or at least one sign of aging in skin; and at least one pharmaceutically or cosmetically acceptable vehicle. In certain embodiments, the composition may further include at least one other plant ingredient or a plant extract, such as a plant extract and/or plant ingredient of *Sesamum*. In the method, the composition is in a product form selected from the group consisting of an aerosol, a cream, a emulsion, a solid, a liquid, a dispersion, a foam, a gel, a lotion, a mousse, an ointment, a powder, a patch, a pomade, a solution, a pump a spray, a stick, a towelette, and combinations thereof. In the method, at least one pharmaceutically or cosmetically acceptable vehicle includes one or more ingredients selected from the group consisting of water, a glycerin, a C1-C4 alcohols, a fatty alcohols, a fatty ethers, a fatty esters, a polyols, a glycols, a vegetable oils, a mineral oils, a liposomes, a laminar lipid materials, a silicone oils, and combinations thereof.

Another embodiment relates to a topical cosmetic composition for improving the appearance of skin or at least one sign of aging in the skin containing one or more cosmetic ingredients selected from the group consisting of alcohols, fats, oils, surfactants, fatty acids, silicone oils, humectants, moisturizers, viscosity modifiers, emulsifiers, stabilizers, coloring agents, and perfumes, where the improvement comprising an amount of a plant ingredient and/or plant extract of *Bauhinia* effective to improve the appearance of skin or at least one sign of aging in skin. In certain embodiments, the topical cosmetic composition may further include at least one other plant ingredient and/or a plant extract, such as a plant extract and/or plant ingredient of *Sesamum*.

Yet another embodiment relates to a method of modulating quinone reductase (QR) protein expression and/or activity in skin cells comprising applying to a skin of a subject a composition in a cosmetically effective amount sufficient to modulate QR protein expression and/or activity in skin cells, wherein the composition comprises an amount of a plant ingredient or plant extract of *Bauhinia*, individually or in combination with an amount of a plant ingredient or plant extract from *Sesamum*, and at least one pharmaceutically or cosmetically acceptable vehicle.

DETAILED DESCRIPTION

Figure 1:
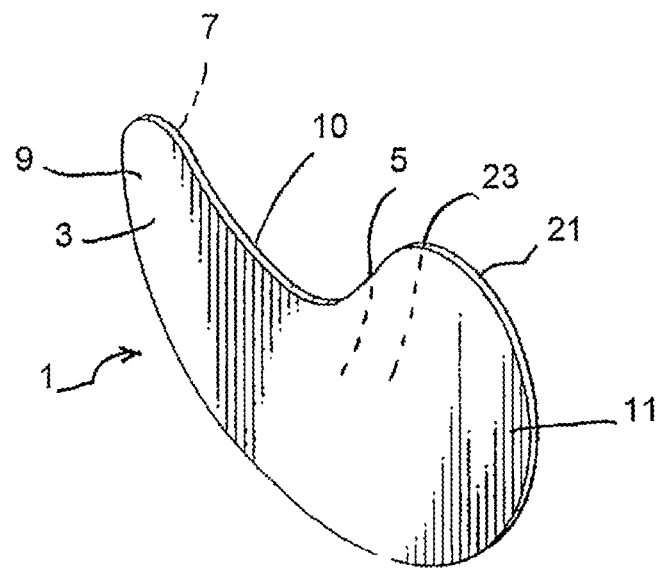
FIG. 1 shows a representative patch for treating an area around the eye.

It is to be understood that this invention is not limited to the particular compositions, methodology, or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular embodiments only, and is not intended to limit the scope of the present invention, which will be limited only by the claims.

As we age, bodily functions begin to deteriorate and operate less efficiently, resulting in greater susceptibility to chronic disease. One theory, the free radical theory of aging, proposes that age-related diseases are due, in part, to increased oxidative damage from free radicals. Free radicals are atoms or molecules with one or more unpaired electrons, which makes them unstable. Because free radicals prefer the stable paired-electron state, they are capable of 'stealing' electrons from nearby molecules, which are damaging critical cellular targets, such as DNA, proteins, and lipids. As a result, there has been increased interest in identifying the targets and effects of free radicals, as well as compounds that can decrease oxidative damage, such as antioxidants.

The present invention is based on the surprising discovery that a plant ingredient and/or a plant extract of *Bauhinia*, individually or in combination with a plant ingredient and/or a plant extract of *Sesamum*, provides an anti-aging skin effect and/or improved aesthetic appearance as well as extending youthfulness of the skin effect. Also, the present invention is based on the surprising discovery that a plant ingredient or plant extract of *Bauhinia*, individually or in combination with a plant ingredient or plant extract from *Sesamum*, prevents, reduces and/or inhibits increased oxidative damage from free radicals, inhibits carbonylation of cells, modulates (e.g., stimulates) phase II detoxifying enzyme NAD(P)H, Quinone oxidoreductase I, also known as Quinone Reductase (QR), and increases anti-oxidant response elements (ARE). The ingredient or extract may be from any species members of genus *Bauhinia* and *Sesamum* groups.

In certain embodiments, surprisingly, when a combination of plant ingredients or plant extracts is used, the anti-aging skin effect may be at least additive, and preferably synergistic, as compared to the effect of the individual botanical components. Accordingly, compositions that include a plant ingredient and/or plant extract of *Bauhinia* and, optionally, a plant ingredient and/or plant extract from *Sesamum*, in sufficient amounts to achieve an anti-aging skin effect and their use are described.

Definitions

The term "composition" refers to a product that treats, improves, promotes, increases, manages, controls, maintains, optimizes, modifies, reduces, inhibits, or prevents a particular condition associated with a natural state, biological process or disease or disorder. For example, a composition improves at least one sign of aging and/or improves the appearance of skin, and the like in a subject. The term composition includes, but is not limited to, pharmaceutical (i.e., drug), over-the counter (OTC), cosmetic, food, food ingredient or dietary supplement compositions that include an effective amount of an extract, at least one component thereof, or a mixture thereof. Exemplary compositions include cream, cosmetic lotion, pack or powder, or as an emulsion, lotion, liniment foam, tablets, plasters, granules, or ointment.

As used herein, the term "extract" or "botanical extract" refers to a solid, viscid, or liquid substance or preparation that includes an active ingredient(s) of a substance of plant, such as *Bauhinia* (e.g., *Bauhinia variegate/purpurea* L; also referred to as Kachnar) and/or *Sesamum* (e.g., *Sesamum indicum*). The ingredient or extract may be from any species members of genus *Bauhinia* and *Sesamum* groups. The term "extract" is intended to include not only a crude extract produced from *Bauhinia* (e.g., *Bauhinia variegate/purpurea* L) and *Sesamum* (e.g., *Sesamum indicum*), and by use of a solvent selected from among water, lower alcohols of 1 to 4 carbon atoms, such as methanol, ethanol, butanol, etc., ethylene, acetone, hexane, ether, chloroform, ethylacetate, butylacetate, dichloromethane, N,N-dimethylformamide (DMF), dimethylsulfoxide (DMSO), 1,3-butylene glycol, propylene glycol and a combination thereof, but also a fraction of the crude extract in such a solvent. So long as it assures the extraction and preservation of the active ingredient(s), any extraction method may be employed. Examples of botanical extracts include extracts from *Bauhinia* (e.g., *Bauhinia variegate/purpurea* L) and *Sesamum* (e.g., *Sesamum indicum*).

As used herein, the term "effective amount" or "therapeutically effective amount" of a pure compound, composition, extract, extract mixture, component of the extract, and/or active agent or ingredient, or a combination thereof refers to an amount effective at dosages and for periods of time sufficient to achieve a desired result. For example, the "effective amount" or "therapeutically effective amount" refers to that amount of a pure compound, composition, extract, botanical extract, extract mixture, botanical extract mixture, component of the extract, and/or active agent or ingredient, or a combination thereof of this invention which, when administered to a subject (e.g., mammal, such as a human), is sufficient to effect treatment, such as improving at least one sign of aging and/or improving the appearance of skin, and the like in a subject by, e.g., preventing, reducing and/or inhibiting increased oxidative damage from free radicals. The amount of a composition, extract, botanical extract, extract mixture, botanical extract mixture, component of the extract, and/or active agent or ingredient of this disclosure that constitutes an "effective amount" or "therapeutically effective treatment" will vary depending on the active agent or the compound, the condition being treated and its severity, the manner of administration, the duration of treatment, or the age of the subject to be treated, but can be determined routinely by one of ordinary skill in the art having regard to his own knowledge and to this disclosure.

"Improving at least one sign of aging" and "improving a sign of aging" are used interchangeably herein to designate preventing, arresting, reversing, ameliorating, diminishing, and/or reducing a sign of aging, especially signs of aging in skin. Representative signs of aging include, but are not limited to, lines, fine lines, wrinkles, crow's feet, dark eye circles, blemishes, age spots, dark spots, stretch marks, or combinations thereof.

"Improving the appearance of skin" and "improving the aesthetic appearance of skin" are used interchangeably herein to designate an aesthetic improvement in the appearance of skin. Representative improvements may include, but are not limited to, favorable characteristics and/or properties related skin thickness, elasticity, resiliency, moisturization, smoothness, tone, texture, radiance, lightness (i.e., skin lightening), luster, brightness, clarity, contour, firmness, tautness, suppleness, softness, sensitivity, pore size, or combinations thereof. These terms may also be used to designate an improvement in an adverse skin condition. Representative adverse conditions affecting by, resulting in or resulting from such an adverse skin condition include, but are not limited to, psoriasis, eczema, seborrhea, dermatitis, sunburn, estrogen imbalance, hyperpigmentation, hypopigmentation, discoloration, yellowing, freckles, skin atrophy, skin breakout, skin fragility, dryness, tactile roughness, chapping, sagginess, thinning, hyperplasia, fibrosis, enlarged pores, cellulite formation, bruising, acne formation, apoptosis, cellular differentiation, cellular de-differentiation, prevention of tumor induction or tumor progression, viral infections, fungal infections, bacterial infections, spider veins (telangectasia), hirsutism, rosacea, pruritis, calluses, warts, corns, or combinations thereof.

The term "pharmaceutically acceptable" means those drugs, medicaments, extracts or inert ingredients, which are suitable for use in contact with the tissues of humans and lower animals without undue toxicity, incompatibility, instability, irritation, and the like, commensurate with a reasonable benefit/risk ratio.

The terms "administer," "administered," "administers" and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In preferred embodiments, topical routes of administering a composition are suitable.

The terms "modulate" or "regulate" refer to ability of a pure compound, composition, extract, extract mixture, component of the extract, and/or active agent or ingredient, or a combination thereof of *Bauhinia* (e.g., *Bauhinia variegate/purpurea* L), individually or in combination with a pure compound, composition, extract, extract mixture, component of the extract, and/or active agent or ingredient, or a combination thereof of *Sesamum* (e.g., *Sesamum indicum* to increase, stimulate or enhance, or decrease, prevent or inhibit expression or activity of a specific molecule. For example, the term "modulate" can refer to ability of *Bauhinia*, individually or in combination with *Sesamum* to decrease increased oxidative damage from free radicals, stimulate Quinone Reductase (QR) activity, and/or increase and/or stimulate anti-oxidant response elements (ARE).

The terms "reduce," "reducing," "inhibit" or "inhibiting" refer to a decrease or reduction in protein activity and/or expression, and/or its downstream effect, in the presence of a plant ingredient or plant extract of *Bauhinia* (e.g., *Bauhinia variegate/purpurea* L), individually or in combination with a plant ingredient or extract from *Sesamum* (*Sesamum indicum*, when compared to protein activity and/or expression in the absence of a plant ingredient or plant extract of *Bauhinia* (e.g., *Bauhinia variegate/purpurea* L), individually or in combination with a plant ingredient or extract from *Sesamum* (*Sesamum indicum*), such as in a control sample. The degree of decrease or inhibition of protein activity and/or expression, and/or its downstream effect, will vary with the nature and quantity of a plant ingredient or plant extract of *Bauhinia* (e.g., *Bauhinia variegate/purpurea* L), individually or in combination with a plant ingredient or extract from *Sesamum* (*Sesamum indicum*) present, but will be evident e.g., as a detectable decrease in protein activity and/or expression; desirably a degree of decrease greater than 10%, 25%, 50%, 75%, 90%, 95% or 99% as compared to protein activity and/or expression in the absence of *Bauhinia*, individually or in combination with a plant ingredient or extract from *Sesamum*.

The terms "increase," "increasing," or "stimulate" refer to an increase in in protein activity and/or expression, and/or its dowstream effect, in the presence of a plant ingredient or plant extract of *Bauhinia* (e.g., *Bauhinia variegate/purpurea* L), individually or in combination with a plant ingredient or extract from *Sesamum* (*Sesamum indicum*), when compared to protein activity and/or expression in the absence of a plant ingredient or plant extract of *Bauhinia* (e.g., *Bauhinia variegate/purpurea* L), individually or in combination with a plant ingredient or extract from *Sesamum* (*Sesamum indicum*), such as in a control sample. The degree of increase of protein activity and/or expression, and/or its downstream effect, will vary with the nature and quantity of a plant ingredient or plant extract of *Bauhinia* (e.g., *Bauhinia variegate/purpurea* L), individually or in combination with a plant ingredient or extract from *Sesamum* (*Sesamum indicum*) present, but will be evident e.g., as a detectable increase in protein activity and/or expression; desirably a degree of increase greater than 10%, 25%, 50%, 75%, 90%, 95% or 99% as compared to protein activity and/or expression in the absence of a plant ingredient or plant extract of *Bauhinia* (e.g., *Bauhinia variegate/purpurea* L), individually or in combination with a plant ingredient or extract from *Sesamum* (*Sesamum indicum*).

As used herein, the term "subject" or "individual" includes mammals to which a composition may be administered. Non-limiting examples of mammals include humans, non-human primates, rodents (including transgenic and non-transgenic mice) or the like. In some embodiments, the subject is a mammal, and in some embodiments, the subject is human.

One embodiment relates to a topical composition that includes an amount of a plant ingredient or plant extract of *Bauhinia* (also referred to as Kachnar) effective to improve the appearance of skin or at least one sign of aging in skin; and at least one pharmaceutically or cosmetically acceptable vehicle. In certain embodiments, the topical composition may further include at least one other plant ingredient or a plant extract, such as a plant extract or plant ingredient of *Sesamum*.

Certain other embodiments relate to a cosmetic treatment system having a topical composition including a plant ingredient, plant extract or a natural complex of *Bauhinia* (e.g., *Bauhinia variegate/purpurea* L), individually or in combination with a plant ingredient or plant extract from *Sesamum* (e.g., *Sesamum indicum*), and a pharmaceutically or cosmetically acceptable vehicle. In certain embodiments, when a combination of plant ingredients or plant extracts is used, the desired effect may be at least additive, and preferably synergistic, as compared to the effect of the individual botanical components.

*Bauhinia* (e.g., *Bauhinia variegate/purpurea* L) is a Hawaiian Orchid, which is native to South China that grows in Hawaii, southern Texas and south-west Florida. *Bauhinia* is known by several names such as Kachnar, Kanchan, Sihappu mantarai, Mountain Ebony, Kovidar, etc.; these names may be used interchangeably throughout the instant specification. It is a small to medium-sized tree growing to 10-12 meters (33-39 ft.) tall, deciduous in the dry season. The leaves are 10-20 centimeters (3.9-7.9 in) long and broad, rounded, and billowed at the base and apex. The flowers are conspicuous, bright pink or white, 8-12 centimeters (3.1-4.7 in) diameter, with five petals. The fruit is a pod 15-30 centimeters (5.9-11.8 in) long, containing several seeds.

*Bauhinia*'s anti-inflammatory and anti-bacterial activities have been previously studied for the use of Asian traditional medicines. As described below, *Bauhinia* has also been found to have AOX (ARE and Quinone Reductase) activity. Furthermore, *Bauhinia* in combination with *Sesamum* showed induction of NRF2, which is a basic leucine zipper (bZIP) protein that regulates the expression of antioxidant proteins that protect against oxidative damage triggered by injury and inflammation.

The botanical extracts of *Bauhinia* and/or *Sesamum* may be commercially obtained from various sources including Barnet Products Corp, Englewood Cliffs, N.J.; Maruzen Pharmaceuticals Co. Ltd, Onomichi-City Hiroshima, Japan; and DSM, Heerlen (NL). In addition, a suitable plant ingredients and botanical extracts of *Bauhinia* and/or *Sesamum* may be obtained using any of the extraction and purification techniques discussed more fully below or known in the art.

In one example, a botanical extract useful in the unique compositions of the present invention might be obtained using an organic solvent extraction technique.

In another example, solvent sequential fractionation may be used to obtain a botanical extract useful in the unique compositions of the present invention.

Total hydro-ethanolic extraction techniques may also be used to obtain a botanical extract useful in the unique compositions of the present invention. Generally, this is referred to as a lump-sum extraction. The botanical extract generated in this process will contain a broad variety of phytochemicals present in the extracted material including fat and water solubles. Following collection of the botanical extract solution, the solvent will be evaporated, resulting in the botanical extract.

Total ethanol extraction may also be used in the present invention. This technique uses ethanol, rather than hydro-ethanol, as the solvent. This extraction technique generates an extract that may include fat soluble and/or lipophilic compounds in addition to water soluble compounds.

Another example of an extraction technique that may be used to obtain an extract useful in the present invention is supercritical fluid carbon dioxide extraction (SFE). In this extraction procedure the material to be extracted is not exposed to any organic solvents. Rather, the extraction solvent is carbon dioxide, with or without a modifier, in supercritical conditions (>31.3° C. and >73.8 bar). Those of skill in the art will appreciate that temperature and pressure conditions can be varied to obtain the best yield of extract. This technique generates an extract of fat soluble and/or lipophilic compounds, similar to the total hexane and ethyl acetate extraction technique described above.

Those of skill in the art will appreciate that there are many other extraction processes, both known in the art and described in various patents and publications that can be used to obtain the extracts to be used in practicing the present invention. For example, the extraction procedures described in the following references, which are incorporated herein by reference, could be used in practicing the present invention: Murga et al., "Extraction of natural complex phenols and tannins from grape seeds by using supercritical mixtures of carbon dioxide and alcohol." *J. Agric Food Chem.* 2000 August: 48(8):3408-12; Hong et al., "Microwave-assisted extraction of phenolic compounds from grape seed." *Nat Prod Lett* 2001; 15(3):197-204; Ashraf-Khorassani et al., "Sequential fractionation of grape seeds into oils, polyphenols, and procyanidins via a single system employing $CO_2$-based fluids." *J. Agric Food Chem.*, 2004 May 5; 52(9):2440-4.

Application of the topical composition of the present invention may improve the aesthetic appearance of the skin, and may rejuvenate or enhance the skin. The compositions of the present invention may also provide a variety of anti-aging and skin texture benefits. It is believed a composition comprising *Bauhinia*, individually or in combination with at least one botanical ingredient or extract, such as *Sesamum* provides significant anti-aging and skin texture benefits relative to other commercially available skin anti-aging topical products. Topical application of the ingredient or combinations of ingredients may produce benefits that are additive or synergistic relative to application of the individual ingredients therein. The terms "synergistic benefit," "synergistic effect," or "synergizing effect" are defined herein as the interaction of two or more combination compositions (e.g., an extract mixture) to produce a combined biological effect(s) or benefit(s) greater than the sum of their separate effects (i.e., 1+1<2 or 1+1+1<3). The synergistic effect can be about or greater than about 10, 20, 30, 50, 75, 100, 120, 150, 200, 250, 350, or 500% or even more than the summed (additive) effect of each composition. The effect can be any of the measurable effects described herein. The term "additive benefit" refers to a combined biological effect(s) or benefit(s) equal to the sum of two or more combination compositions (e.g., an extract mixture) separate effects.

The composition comprising *Bauhinia*, individually or in combination with a botanical ingredient or extract of *Sesamum* provides benefits to skin relating to anti-aging and improved aesthetic appearance. Accordingly, certain embodiments relate to topical compositions and methods for their use in treating skin to prevent, arrest, reverse, ameliorate, diminish, reduce or improve signs of aging, including, or associated with, chronological aging, hormonal aging, and/or photoaging. The signs of aging may include, but are not limited to, skin fragility; loss of collagen and/or elastin; estrogen imbalance in skin; skin atrophy; appearance and/or depth of lines and/or wrinkles, including fine lines; skin discoloration, including dark eye circles; crow's feet; skin sagging; skin fatigue and/or stress, e.g., skin breakout due to environmental stress, such as pollution and/or temperature changes; skin dryness, fine lines due to skin dryness, skin roughness; skin flakiness; cellular aging; loss of skin tone, elasticity, clarity, luminosity, and/or luster; loss of skin firmness; poor skin texture; loss of skin elasticity and/or resiliency; thin skin, and inflammation.

The benefits and improvements to the aesthetic appearance of skin can be manifested in any of the following: reduction in pore size, fine lines, wrinkles, tactile roughness, and inflammation; improvement in skin tone, radiance, clarity and/or tautness; promotion of anti-oxidant activity; improvement in skin firmness, plumpness, suppleness, and/or softness; improvement in procollagen and/or collagen production; improvement in skin texture and/or promotion of retexturization; improvement in skin barrier repair and/or function; improvement in appearance of skin contours; restoration of skin luster, clarity, and/or brightness; replenishment of essential nutrients and/or constituents in the skin decreased by aging and/or menopause; improvement in communication among skin cells; increase in cell proliferation and/or multiplication; increase in skin cell metabolism decreased by aging and/or menopause; improvement in skin moisturization; promotion and/or acceleration of cell turnover; enhancement of skin thickness; increase in skin elasticity and/or resiliency; and enhancement of exfoliation, with or without the use of alpha or beta hydroxy acids, keto acids or other exfoliants.

Other benefits may include an increase in skin smoothness and/or softness, an increase in the perception of skin condition, an increase in skin moisture, a reduction in skin stress and fine lines, an increase in brightness and/or lightening, improved skin texture and skin firmness.

In one embodiment of the present invention, the topical composition includes *Bauhinia* in the amount sufficient to provide benefits to skin relating to anti-aging and improved aesthetic appearance; and a pharmaceutically or cosmetically acceptable vehicle. Specifically, *Bauhinia* is present in an amount ranging from about 0.0001% to 5% by weight of the total composition, desirably from about 0.001 wt % to about wt 0.5%, more desirably from about 0.01 wt % to about 0.1 wt %.

In certain embodiments, the compositions including a plant ingredient, a plant extract or a natural complex of *Bauhinia* may also include a plant ingredient or plant extract from *Sesamum*. The ingredient or extract may be from any species members of these genus groups.

Certain other embodiments relate to a the topical composition that includes *Bauhinia* in combination with at least one other plant ingredient or plant extract, such as *Sesamum*, in the amounts sufficient to provide benefits to skin relating to anti-aging and improved aesthetic appearance; and a pharmaceutically or cosmetically acceptable vehicle.

In a particular embodiment, the topical composition may include *Bauhinia* in combination with *Sesamum*. The plant ingredients or plant extracts in combination with *Bauhinia* for use in the present invention are generally present in the composition, individually or collectively, in an amount ranging from about 0.0001% to 5% by weight of the total composition, desirably from about 0.001 wt % to about wt 0.5%, more desirably from about 0.01 wt % to about 0.1 wt %.

A particularly preferred embodiment relates to a cosmetic treatment system utilizing a topical composition suitably formulated for treatment of the area around the eyes. While not wishing to be bound by theory, it is believed treatment of the eye area can be improved when using a patch impregnated with a composition comprising *Bauhinia*, individually or in combination with at least one plant ingredient or plant extract, such as *Sesamum*.

The compositions may have a pH between about 6.0 to about 8.0, or alternatively the composition may have a pH that is substantially neutral. In certain embodiments, the compositions in which the botanical extract is used have a generally neutral pH.

In certain other embodiments, the composition of the present invention can further include DNA repair enzymes. DNA repair enzymes for use in the present invention may include enzymes involved in either the base excision repair (BER), the nucleotide excision repair (NER) pathway, or alternate excision repair pathways as described in e.g., U.S. Pat. No. 6,368,594. These pathways are mediated by separate sets of proteins capable of carrying out DNA incision, lesion removal, gap-filling, and ligation reactions.

The NER pathway constitutes a widely distributed, lesion non-specific repair pathway orchestrating DNA damage removal via a dual incision reaction upstream and downstream from the damage site resulting in release of an oligonucleotide containing the damage. Following removal of the damaged DNA, the resulting gap is filled and the DNA ends are ligated together.

The BER pathway is the primary defense against all major forms of DNA base damage. This pathway is responsible for detecting and removing a variety of specific, individual base lesions within a large pool of undamaged DNA. BER pathways typically involve the activity of N-glycosylase/AP lyase enzymes specific for CPDs. The N-glycosylase/AP lyase enzymes first cleave the N-glycosidic bond of a CPD 5' pyrimidine and then cleave the phosphodiester backbone at an abasic site via a β-lyase mechanism.

Suitable DNA repair enzymes for use in the present invention have N-glycosylase/AP lyase activities capable of recognizing, excising and repairing damaged DNA, such as CPDs and (6-4) photoproducts. The activity of these enzymes can be light-dependent (e.g., photolyases) or light-independent. Exemplary DNA repair enzymes in this group include, but are not limited to, bacteriophage T4 pyrimidine dimer-specific endonuclease (deny endonuclease), *Micrococcus luteus* N-glycosylase/AP lyase, *Saccharomyces cerevisiae* N-glycosylase/apurinic-apyrimidinic lyase, *Schizosaccharomyces pombe* UV damage endonuclease (UVDE), *Chlorella* virus isolate PBCV-1 pyrimidine dimer-specific glycosylase, *Anacystis nidulans* photolyase, and modified, non-native (e.g., recombinant) enzyme products thereof.

DNA repair enzymes may also include other members from the BER, NER or alternate pathways. These enzymes may include $O^6$-methylguanine-DNA methyltransferases, uracil- and hypoxanthine-DNA glycosylases, DNA exonucleases, damaged-bases glycosylases (e.g., 3-methyladenine-DNA glycosylase), endonucleases alone or in complexes (e.g., *E. coli* uvrA/uvrB/uvrC endonuclease complex), and other enzymes and enzyme complexes whose activities at present are only partially understood, such as, the products of the ERCC genes of humans and the RAD genes of yeast. Exemplary DNA repair enzymes include, but are not limited to, uracil DNA glycosylases, 3-methyladenine DNA glycosylase, Endonuclease III/thymine glycol DNA glycosylases, Endonuclease VIII, fapy/8-oxoguanine DNA glycosylases, A-G-mismatch DNA glycosylases, G-T mismatch DNA glycosylases, formyluracil DNA glycosylases, hydroxymethyl uracil DNA glycosylases, XPC-hHR23B, XPA, RPA, XPB, TFIIH, XPG, XPF-ERCC1, Rad-4-Rad23, Rad14, Rfa, Rad25/Ss12, Rad3, Rad2, Rad1-Rad10, various DNA polymerases, DNA ligases and the like. Exemplary sources for these enzymes may include bacterial or mammalian cell sources, including, but not limited to *E. coli, S. cerevisiae, S. pombe*, human, human, monkey, mouse, rat, hamster and the like.

As used herein, the term "DNA repair enzyme" is intended to include the foregoing enzymes and other enzymes now known or subsequently discovered or developed, including glycosylases, apurinic/apyrimidinic endonucleases or other enzymes having activities capable of repairing damaged DNA.

DNA repair enzymes may be derived or extracted from suitable sources such as *E. coli, Micrococcus*, and the like. The DNA repair enzymes may be encapsulated in liposomes as described in U.S. Pat. No. 5,296,231, the entire content of which is incorporated herein by reference. For example, a DNA repair enzyme derived from a *Micrococcus luteus* cell lysate is provided in a liposomal formulation containing lecithin and water and is available as ULTRASOMES™ from Applied Genetics, Inc. Dermatics, Freeport, N.Y. or ULTRASOMES-V™ from Barnet Products Corporation, Englewood Cliffs, N.J. Liposomes encapsulating an *Anacystis nidulans* lysate containing the *Anacystis nidulans* photolyase are available as PHOTOSOMES™ or PHOTOSOMES-V™ from Applied Genetics, Inc. Dermatics, (Freeport, N.Y.). The liposomes may include conventional phospholipids, oleic acid and/or cholesterol hemisuccinate from vegetable-derived sources, e.g., soybean or they may be produced from other suitable sources conventionally known to those skilled in the art.

Exemplary embodiments may incorporate ULTRASOMES™, ULTRASOMES-V™, PHOTOSOMES™, or PHOTOSOMES-V™ in an amount ranging from about 0.01% to 20% by weight of the total composition, desirably from about 0.1 wt % to about wt 10%, more desirably from about 0.5 wt % to about 3 wt %.

Liposomes may be used as delivery agents to facilitate transfer of cosmetically active agents into the dermis of skin, such as the DNA repair enzymes or the plant or botanical ingredients of the present invention. Other delivery agents may be used for dermal delivery in place of the liposomes, including, but not limited to skin delivery vehicles known to those skilled in the art, including emulsions, microemulsions, nanoemulsions, nanoparticles, microspheres, ethosomes, transfersomes, and niosomes.

In certain embodiments, additional cosmetic ingredients may also be included in the cosmetic composition, including, but not limited to, ingredients present in: licorice, licorice extracts, licorice derivatives (e.g., glycyrrhizinates); lemon extract; cucumber extract; sunflower seed extract; castor seed oil; oat proteins, oat extracts, hydrolyzed oats; silk protein (e.g., sericin); hyaluronic acid and its derivatives (e.g., sodium hyaluronate); vitamins; minerals; anti-oxidants; phospholipids, sphingolipids, cholesterol; and/or other ingredients or combinations thereof having anti-aging, anti-oxidant, anti-inflammatory, anti-irritant, anti-cancer or other skin-protective properties; aesthetic appearance enhancing properties; and/or increased skin delivery properties.

Cosmetically useful vitamins, minerals and/or anti-oxidants for topical application in accordance with the present invention include plant ingredients and extracts having anti-oxidant properties (e.g., Rosemary extract, *Centella asiaticoside*, etc.); vitamin A and its precursors or derivatives (e.g., beta-carotene, retinyl palmitate); vitamin B3 and its precursors or derivatives (e.g., niacinamide); vitamin B5 and its precursors or derivatives (e.g. panthenol); vitamin C and its precursors or derivatives (e.g., tetrahexyldecyl ascorbate, ascorbyl palmitate); vitamin E and its precursors or derivatives (e.g., d-alpha-tocopherol, tocopheryl acetate); vitamin K and its precursors or derivatives; selenium and its derivatives (e.g., L-selenomethionine); and alpha lipoic acid (ALA).

ALA is a potent, naturally occurring anti-oxidant, sometimes referred to as the "universal anti-oxidant" because of its activity and solubility in both water and lipids. ALA is able to penetrate into skin cells, is able to prevent activation of the proinflammatory NF-kB pathway responsible for breakdown of collagen and elastin, and is able to boost the protective effects of vitamins E and C, thereby boosting naturally occurring anti-oxidants within cells.

In one embodiment, tetrahexyldecyl ascorbate may be incorporated in the composition of the present invention. Tetrahexyldecyl ascorbate is a stable, lipid-soluble ester derivative of vitamin C. Vitamin C has been reported to promote collagen synthesis, inhibit lipid breakdown, regenerate vitamin E, reduce fine lines and wrinkles, heal sunburns, and is a potent anti-oxidant scavenger of free radicals having significant anti-inflammatory properties, hindering production of e.g., arachidonic acid.

In another embodiment, panthenol or its equivalents are contemplated for use with the composition. Panthenol is an effective film-forming moisturizing agent having anti-inflammatory properties. Panthenol equivalents may include alcohol derivatives of pantothenic acid, such as the ones described in CTFA Cosmetic Ingredient Handbook, The Cosmetic, Toiletry and Fragrance Association. Inc., pp. 272-273, 1992. For optimal usefulness, the amount of panthenol should be chosen so that the composition dries reasonably quickly. The more panthenol in the composition, the longer it takes for the composition to dry when it is applied to skin or other surfaces.

Vitamins, minerals, and/or anti-oxidants may be present in a collective amount ranging from about 0.01% to 20% by weight of the total composition, desirably from about 0.1 wt % to about wt 10%, more desirably from about 0.5 wt % to about 3 wt %.

Optionally, the present composition may additionally include one or more anesthetics, anti-allergenics, anti-irritants, antifungals, anti-microbials, anti-inflammatory agents, antiseptics, chelating agents, colorants, depigmenting agents, emollients, emulsifiers, film formers, fragrances, humectants, insect repellents, lubricants, moisturizers, pharmaceutical agents, photostabilizing agents, preservatives, skin protectants, skin penetration enhancers, sunscreens, stabilizers, surfactants, thickeners, viscosity modifiers, or any combinations thereof.

Certain embodiment relate to plant or botanical ingredients and natural, active ingredients having anti-irritant or anti-inflammatory properties to counter potential irritation to skin. Although some embodiments lack the use of exfoliating agents, these agents may be included provided that sufficient anti-irritant/anti-inflammatory agents are included to ameliorate the irritating effects of exfoliating agents. Exemplary anti-irritants include, but are not limited to, aloe vera, a-bisabolol, caffeine or other xanthenes, chamomile, cola nitada extract, dipotassium glycyrrhizinate, glycyrrhizic acid and its derivatives, green tea extract, lecithin or hydrogenated lecithin, licorice extract, tea tree oil, steroidal or non-steroidal anti-inflammatory agents, including, but not limited to cyclooxygenase inhibitors (e.g., salicylic acid, acetylsalicylic acid), NF-KB inhibitors, strontium acetate, strontium chloride, strontium nitrate, urea, or combinations thereof. Desirable anti-irritants may include dipotassium glycyrrhizinate, lecithin and hydrogenated lecithin.

Anti-irritant or anti-inflammatory agents may be present individually or collectively in an amount ranging from about 0.01% to 10% by weight of the total composition, desirably from about 0.05 wt % to about 5 wt %, more desirably from about 0.2 wt % to about 1.5 wt %.

The plant ingredients, plant extracts, oils, vitamins, minerals, antioxidants, anti-irritants or other active agents may be included, either individually or collectively, in a pharmaceutically or cosmetically acceptable vehicle. Examples of pharmaceutically or cosmetically acceptable vehicles suitable for the embodiments of the present invention include, but are not limited to, water, C1-C4 alcohols, fatty alcohols, fatty ethers, fatty esters, glycerin, glycols, vegetable oils, mineral oils, lecithin, hydrogenated lecithin, liposomes, laminar lipid materials, phospholipids, polyglycols, polyols, propyl alcohol, silicone oils, vegetable oil, or any combinations thereof.

The pharmaceutically or cosmetically acceptable vehicle for use with the compositions of the present invention may be in the form of a homogeneous phase formulation or in the form of an emulsion or microemulsion including, but not limited to, oil-in-water, water-in-oil and multiple including triple, phase emulsions. These emulsions can cover a broad range of consistencies including thin lotions (which can also be suitable for spray or aerosol delivery), creamy lotions, light creams and heavy creams. Other suitable topical carriers include anhydrous liquid solvents such as oil and alcohol; aqueous-based single phase liquid solvent (e.g., hydro-alcoholic solvent system); anhydrous solid and semisolid (such as gel and stick); and aqueous based gel and mousse system.

The pharmaceutically or cosmetically acceptable vehicle will usually contain from about 5% to about 99.9% by weight of the total composition, desirably from about 25% to about 80%, and more desirably from about 50% to about 70% by weight of the composition, and may, in the absence of other cosmetic adjuncts, form the balance of the composition.

Emollients are moisturizers to maintain hydration or to rehydrate the skin by providing a protective emollient coating. Emollients may be classified under such general chemical categories as esters, fatty acids and alcohols, polyols and hydrocarbons. Esters may be mono- or di-esters. Representative examples of fatty di-esters include, but are not limited to, dipotassium glycyrrhizinate, dibutyl adipate, diethyl sebacate, diisopropyl dimerate, and dioctyl succinate. Acceptable branched chain fatty esters include, but are not limited to, 2-ethyl-hexyl myristate, isopropyl stearate and isostearyl palmitate. Acceptable tribasic acid esters include, but are not limited to, triisopropyl trilinoleate and trilauryl citrate. Acceptable straight chain fatty esters include, but are not limited to, lauryl palmitate, myristyl lactate, and stearyl oleate.

Suitable fatty alcohols and acids may include, but are not limited to, alcohols or acids having from about 10 to 20 carbon atoms. For example, alcohols such as cetyl, myristyl, palmitic and stearyl alcohols and acids may be used.

Polyols may serve as emollients, including, but not limited to linear and branched chain alkyl polyhydroxyl compounds. Representative polyols, include, but are not limited to butylene, propylene glycol, sorbitol, glycerin, polymeric polyols, such as polypropylene glycol and polyethylene glycol, and the like.

Hydrocarbons may serve as emollients and may include hydrocarbon chains having from about 12 to 30 carbon atoms, including, but not limited to mineral oil, petroleum jelly, squalene and isoparaffins.

Exemplary emollients include, but are not limited to, butylene, caprylic/capric triglyerides, castor oil, ceteareth-20, ceteareth-30, cetearyl alcohol, ceteth 20, cetostearyl alcohol, cetyl alcohol, cetyl stearyl alcohol, cholesterol, cocoa butter, diisopropyl adipate, glycerin, gyceryl monooleate, glyceryl monostearate, glyceryl stearate, isoparaffins, isopropyl myristate, isopropyl palmitate, lanolin, lanolin alcohol, hydrogenated lanolin, isoparaffins, liquid paraffins, linoleic acid, mineral oil, oleic acid, petroleum jelly, phospholipids, polyethylene glycol, polyethylene glycol-7 glyceryl cocoate, polyethylene glycol-18 methyl ester dimethyl silane, polyoxyethylene glycol fatty alcohol ethers, polyoxypropylene 15-stearyl ether, polypropylene glycol propylene glycol, propylene glycol stearate, sorbitol, sphingolipids, squalene, steareth-2 or -100, stearic acid, stearyl alcohol, urea, white petrolatum, and the like.

Emollients may be present individually or collectively in an amount ranging from about 0.005% to 20% by weight of the total composition, desirably from about 0.1 wt % to about 10 wt %, more desirably from about 1.0 wt % to about 5.0 wt %.

Humectants are moisturizers that can bind water and retain it on the skin surface. Exemplary humectants include, but are not limited to, acetyl glucosamine, bisaccharide gum, butylene glycol, ethoxydiglycol, ethylene glycolpolypropylene, glucose, glycereth-26, glycerin, glycerol, glycol, lactitol, maltitol, propylene glycol, sericin, sodium hyaluronate, sorbitol, xylitol, sodium citrate, glucose and the like.

Humectants may be collectively present in an amount ranging from about 0.1% to 40% by weight of the total composition, desirably from about 2.5 wt % to about wt 25%, more desirably from about 5 wt % to about 15 wt %.

The present compositions may provide one or more preservatives. Suitable preservatives include disodium EDTA, benzyl alcohol, methylparaben, phenoxyethanol, propylparaben, ethylparaben, butylparaben and isobutylparaben.

Another category of functional ingredients within the cosmetic compositions of the present invention are thickeners. Thickeners will usually be present in a collective amount ranging anywhere from about 0.01 to 10% by weight, desirably from about 0.05 to 5% by weight, more desirably from about 0.1% to 1% by weight of the composition. Exemplary thickeners are cross-linked polyacrylate materials. Gums such as xanthan, carrageenan, gelatin, karaya, pectin and locust bean gum may be used. Under certain circumstances the thickening function may be accomplished by a material also serving as a silicone or emollient. For instance, silicone gums in excess of 10 centistokes and esters such as glycerol stearate have dual functionality.

In certain embodiments skin whitening agents may be included in the compositions of the present invention. Skin whitening agents include but are not limited to tyrosinase inhibitors, free radical scavengers, and mixtures thereof.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

The compositions of the present invention may be formulated in any convenient form suitable for topical application to the skin. Such product forms include, but are not limited to, aerosol spray, cream, dispersion, emulsion, foam, gel, liquid, lotion, mousse, ointment, patch, pomade, pack or powder, pump spray, solid, solution, stick, and towelette. A desired cosmetic form is a cream that is an oil-in-water emulsion. Water-in-oil and water-in-silicone emulsions also are contemplated. In each formulation, various known conventional cosmetic ingredients may be incorporated. For example, cosmetic ingredients such as alcohols, fats and oils, surfactants, fatty acids, silicone oils, humectants, moisturizers, viscosity modifiers, emulsifiers, stabilizers, coloring agents, and perfumes may be included. The compositions may be administered as needed, daily, several times per day or in any suitable regimen such that the desired outcome is achieved. The compositions may be administered on a continuous basis or intermittent basis.

Certain embodiments relate to a cosmetic treatment system including a patch impregnated with the topical composition of the present invention. Patches for use in the present invention may come in any shape suitable for treating a particular target area. The patch may encompass a small area targeting a particular area or it may cover a large area, such as a face in the form of a mask. The overall size and geometry of current patches for applying medicaments around the eyes can make it difficult to apply eye treatment products in close proximity to the eye.

FIG. 1 depicts a representative patch 1 of the present invention. The patch includes a front side 3 and a back side 7 impregnated with the topical composition 5. When treating the eye area, the patch 1 may be kidney-shaped with convex ends, a smaller radiused first end 9, and a larger radiused second end 11 opposite the first end 9 with a top portion 10 having a surface that is substantially parallel to the curvature of the cheekbone adjacent to a subject's eye. The relatively shorter, more radiused design of the eye patch 1 depicted in FIG. 1 makes it easier for a subject 13 to position the patch 1 in close proximity to the eye 15, both under the eye 17 and near the side of the eye 19. However, for treatment of the area around the eye, the length, width, and geometry of the patch 1 set forth in e.g., FIG. 1 may be varied without negatively impacting its effectiveness. Moreover, the present invention may include a pair of patches 1 for treating each eye 15 individually, or it may contain a single, continuous patch for treating both eyes at once. A patch 1 for use with the present invention may be further adapted, fitted and/or cut in accordance to the particular contours or shape of the area to be treated. A skilled artisan will of course recognize that the front side 5 or the back side 7 of patch 1 may be impregnated with the topical composition 5, depending on the orientation of the patch 1 or the particular eye that is being treated.

The patch 1 may be made of any removal material suitable for absorbing, containing, and releasing compositions of the present invention. For example, the patch 1 may be made of non-woven material. The non-woven material may include cotton, cotton/polyester blends, or other suitable combinations of natural or synthetic materials. The patch may be further adapted to provide an occlusive, semi-occlusive or non-occlusive barrier. The patch may be adhesive or non-adhesive. As depicted in FIG. 1, the patch 1 may include a single layer of material 21 or it may include multiple layers of the same and/or dissimilar materials to provide additional structural integrity and/or flexibility. Suitable patches or patch materials are disclosed in e.g., U.S. Pat. Nos. 6,096, 334; 6,120,792; 6,495,158; 6,623,751; 8,697,099; U.S. Pat. Appl. No. 2002/0086043; U.S. Pat. Appl. No. 2003/0152610; U.S. 2003/0175328; and references cited therein, the contents of which are incorporated herein by reference.

The topical composition 5 may be coated onto at least a portion of the patch 1 immediately prior to applying the patch 1 to a subject 13. Alternatively, the patch 1 may be pre-coated with the topical composition and ready for use. Preferably, the topical composition 5 is applied to substantially the entire surface back 7 of the patch 1. The patch 1 and/or the topical composition 5 may further include an adhesive 23. The adhesive 23 may be applied to the back 7 of the patch 1 prior to or subsequent to applying the topical composition 5 to the patch 1. The adhesive 23 may be any adhesive known to those skilled in the art and suitable for removably adhering the patch and/or topical composition to a substrate, such as human skin. The adhesive may be applied to the front side 5 or the back side 7 of patch 1, depending on the orientation of the patch 1 or the particular side impregnated with the topical composition.

The cosmetic treatment system of the present invention may include a packaging system for holding the individual components of the cosmetic treatment system. In a preferred embodiment, the cosmetic treatment system includes a patch; at least one container; and a topical composition formulated for treatment of an area in close proximity to the eye.

Figure 3:
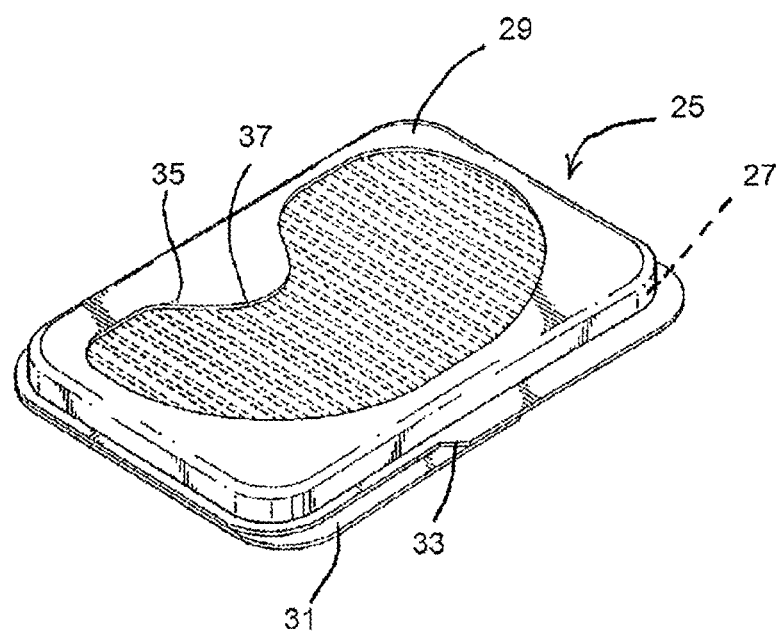
FIG. 3 shows a representative container for holding the patch of FIG. 1.

One or more containers may be used to hold one or more of the components of the cosmetic treatment system. Any container(s) suitable for holding the components of the cosmetic treatment system may be used in accordance with conventional practices known to those skilled in the art. FIG. 3 depicts a representative container 25 adapted for holding the patch 1. The rectangular container 25 includes an interior 27, a top cover 29 and a base portion 31. The top cover 29 may include an indent 33 for opening or separating the top cover 29 from the base portion 31, to facilitate retrieval of the patch 1 held in place by a sunken cavity having a sufficient depth 35 and shape 37 complementarily adapted for securely holding the patch 1 of FIG. 1 in the base portion 31. Alternatively, the patch may be packaged in a container in the form of a sunken tray overlayed with a sealably removable cover to securely maintain the patch in the sunken tray prior to use.

Figure 2:
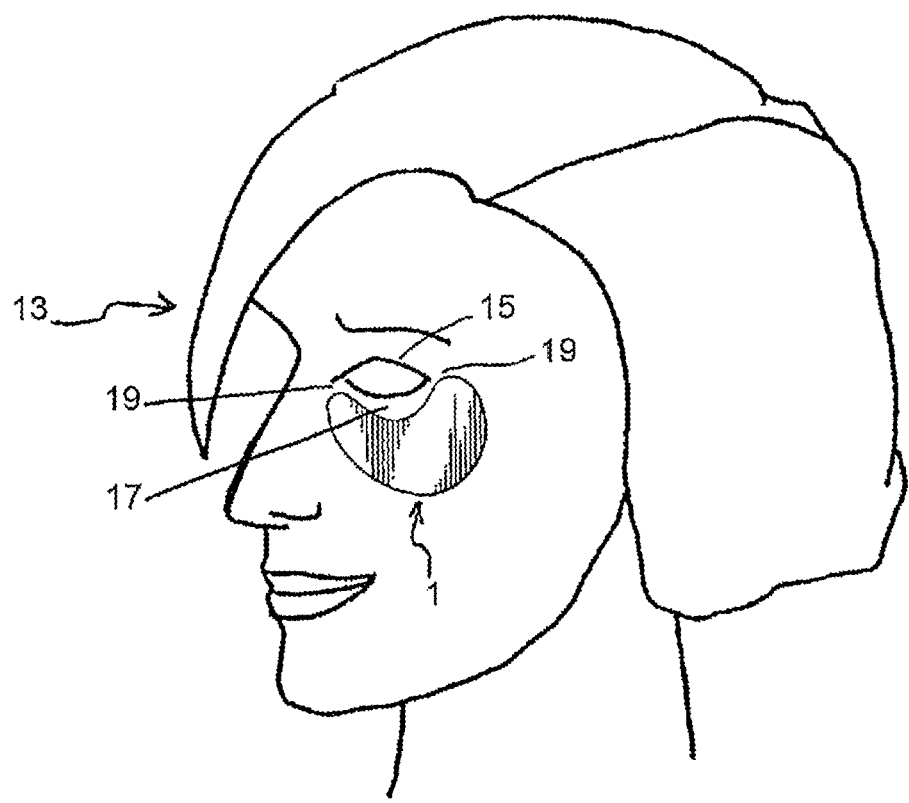
FIG. 2 shows the patch of FIG. 1 affixed to a portion of a subject's face under the subject's left eye.

The container may be prepared by thermoforming or by thin-wall injection molding of a suitable material, such as polypropylene. The design of the container 25 can be modified and adapted to the shape of the particular patch. The container 25 may be formulated for holding only the patch or it may be formulated to hold the patch 1, as well as the other components of the cosmetic treatment system, including the topical composition 5 and/or an adhesive 23 for promoting the adherence of the topical composition 5 and/or patch 1 to a subject 13 as exemplified in FIG. 2. Suitable containers for holding patches of the present invention are disclosed in U.S. Pat. No. 6,623,751, the contents of which are incorporated herein by reference.

Certain embodiments relate to topical composition(s) that may be packaged in a suitable container to suit its viscosity and intended use by the consumer. For example, a lotion or a cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. In certain embodiments, a closed container containing a cosmetically acceptable composition as herein defined may be used.

Certain further embodiments relate to a cosmetic treatment system including a packaging system containing a suitable amount of the cosmetic composition suitable for a desired period of time, such as fourteen days. According to this embodiment, the cosmetic treatment system includes a packaging system containing a plurality of containers, with each container having an amount of the cosmetic composition according to the present invention suitable for a single use. The container may be in the form of a vial or other suitable holding device.

In one embodiment, the cosmetic treatment system includes a packaging system having a plurality of vials, each vial containing a sufficient amount of the cosmetic composition suitable for a single application of the cosmetic composition to the skin. The packaging system may be formulated to provide a number of vials matching the number of days in which the cosmetic composition is applied to skin. Alternatively, the packaging system may be formulated for more than one application per day. In one embodiment, the packaging system may contain 14 vials for daily treatment to skin over a period of 14 days. The packaging system may further contain one or more applicators for applying the compositions and may further include a set of instructions for use of the packaging system associated with the cosmetic treatment system.

The present invention also includes methods of treating skin by topically applying the cosmetic compositions of the present invention. In use, a small quantity of the composition, for example from 0.1 to 100 mL, may be applied to exposed areas of the skin, from a suitable container or applicator and, if necessary, it is then spread over and/or rubbed into the skin using the hand or fingers or a suitable device. Alternatively, the composition may be applied to the skin in the form of a patch that has been impregnated with the composition. The patch may be made of non-woven material and may further contain an adhesive to adhere the patch to the skin.

Certain embodiments relate to a method for preventing, arresting, reversing, ameliorating, diminishing, reducing or improving a sign of aging, in which a composition of the present invention is topically applied to skin in a cosmetically effective amount sufficient to prevent, arrest, reverse ameliorate, diminish, reduce or improve a sign of aging in skin. Exemplary signs of aging include, but are not limited to, facial lines, fine lines, wrinkles, crow's feet, dark eye circles, blemishes, age spots, stretch marks, or combinations thereof.

Certain other embodiments relate to a method for improving the aesthetic appearance of skin, in which a composition of the present invention is topically applied to skin in a cosmetically effective amount sufficient to improve the aesthetic appearance of the skin. The improvements may relate to skin thickness, elasticity, resiliency, moisturization, tone, texture, radiance, luster, lightening, brightness, clarity, contour, firmness, tautness, suppleness, softness, sensitivity, pore size, or combinations thereof.

The improvements may further relate to improving adverse skin conditions affected by, resulting in or resulting from the group consisting of psoriasis, eczema, seborrhea, dermatitis, sunburn, estrogen imbalance, hyperpigmentation, hypopigmentation, discoloration, yellowing, freckles, skin atrophy, skin breakout, skin fragility, dryness, chapping, sagginess, thinning, hyperplasia, fibrosis, enlarged pores, cellulite formation, bruising, acne formation, apoptosis, cellular differentiation, cellular de-differentiation, prevention of tumor induction or tumor progression, viral infections, fungal infections, bacterial infections, spider veins (telangectasia), hirsutism, rosacea, pruritis, calluses, warts, corns, or combinations thereof.

The signs of aging or adverse skin conditions may result from free radical damage, environmental agents, pollutants, diet, chronological aging, premature aging, hormonal aging, photo-aging, or combinations thereof. Accordingly, the present compositions and methods selected for improved anti-aging characteristics or adverse skin conditions may employ topical application of active ingredients inhibiting enzymes or mediators that accelerate or facilitate aging, damage, formation of free radicals, or breakdown of skin elements, including, but not limited to metalloproteinases, collagenases, elastases, hyaluronidases, and proteases. The active ingredients may have anti-oxidant activity, free radical scavenging or anti-inflammatory activity and/or they may inhibit breakdown of collagen, elastin, fibronectin, hyaluronic acid, glycosaminoglycans (GAG) or other extracellular matrix elements or regulatory enzymes or mediators of the NF-kB signal transduction pathway. The active agents may also inhibit other signal transduction pathways associated with aging, including the mediators and regulators associated with these pathways, or combinations thereof.

In certain embodiments, the active agent(s) may also modulate Quinone Reductase (QR) (i.e., promote high QR activity) thus prevent oxidative damage and/or increase anti-oxidant response elements (ARE).

Figure 4:
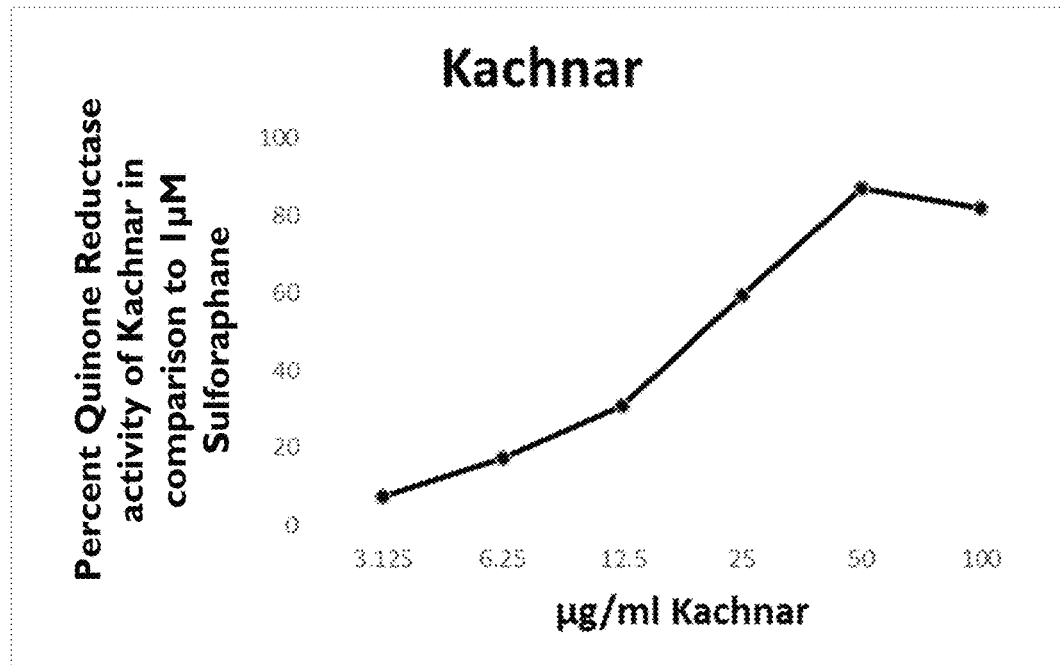
FIG. 4 show dose-dependent stimulation of Quinone Reductase activity by Kachnar in comparison with 1 µM Sulforaphane.

Certain embodiments relate to a method of modulating Quinone Reductase expression and/or activity in a skin cell comprising applying to a skin of a subject a composition in a cosmetically effective amount sufficient to modulate Quinone Reductase protein expression and/or activity the skin, wherein the composition comprises an amount of a plant ingredient or plant extract of *Bauhinia*, individually or in combination with an amount of a plant ingredient or plant extract of *Sesamum*, and at least one pharmaceutically or cosmetically acceptable vehicle. As shown in FIG. 4, Kachnar stimulated Quinone Reductase activity confirming strong anti-oxidant activity of Kachnar.

Figure 6:
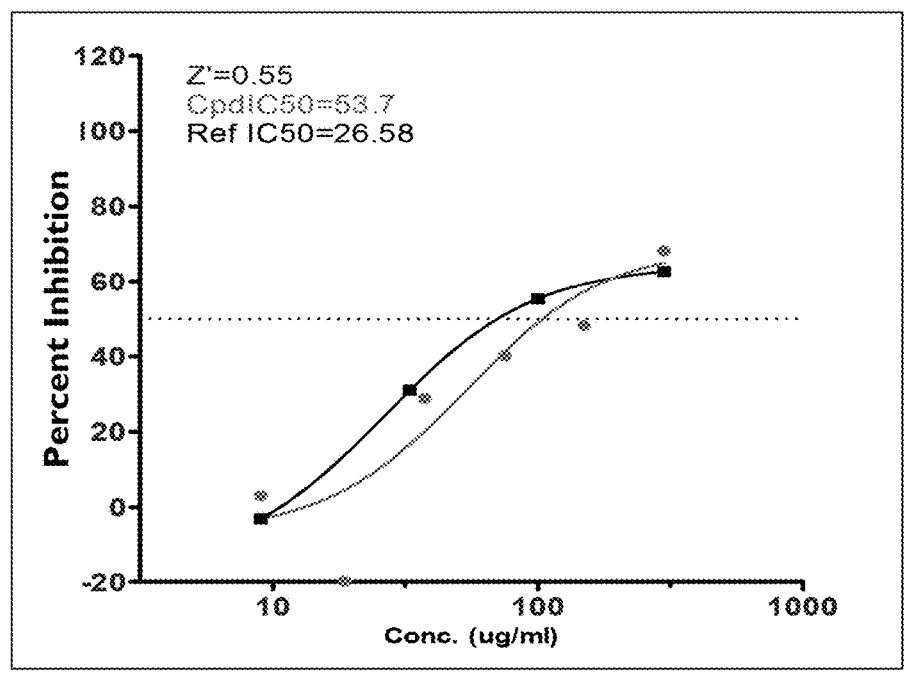
FIG. 6 shows a graph showing carbonylation inhibition of Kachnar as compared to Vitamin C in HepG2 cells.

Further embodiments relate to a method of preventing or inhibiting carbonylation in skin cells comprising applying to a skin a composition in a cosmetically effective amount sufficient to prevent or inhibit carbonylation in the skin, wherein the composition comprises an amount of a plant ingredient or plant extract of *Bauhinia*, individually or in combination with an amount of a plant ingredient or plant extract of *Sesamum*, and at least one pharmaceutically or cosmetically acceptable vehicle. As shown in FIG. 6, Kachnar inhibited carbonylation in HepG2 cells.

Figure 7:
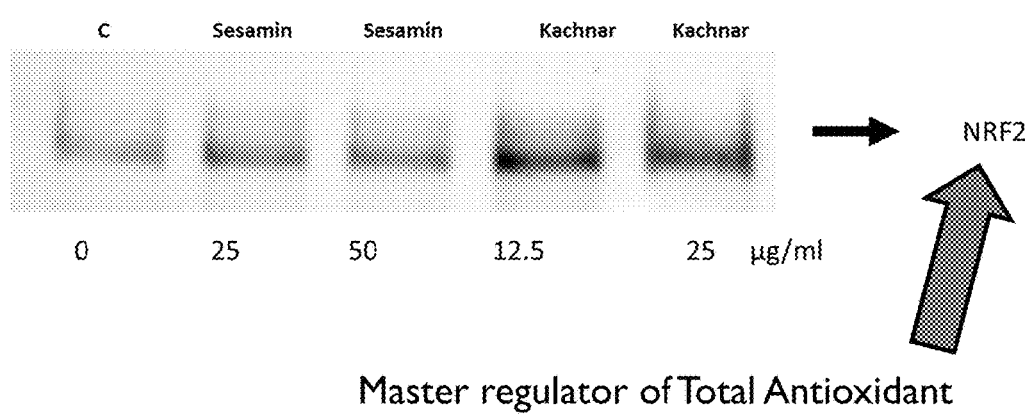
FIG. 7 shows a picture of a Western blot results showing induction of RF2 by Sesamin and Kachnar.

Further embodiments relate to a method of increasing NRF2 in skin cells comprising applying to a skin a composition in a cosmetically effective amount sufficient to increase NRF2 in the skin, wherein the composition comprises an amount of a plant ingredient or plant extract of *Bauhinia*, individually or in combination with an amount of a plant ingredient or plant extract of *Sesamum*, and at least one pharmaceutically or cosmetically acceptable vehicle. As shown in FIG. 7, Kachnar increased protein expression of NRF2, which is a master regulator of total anti-oxidant.

Another embodiment relates to a method of increasing ARE response in a skin cell comprising applying to the skin a composition in a cosmetically effective amount sufficient to increase ARE response in the skin, wherein the composition comprises an amount of a plant ingredient or plant extract of *Bauhinia*, individually or in combination with a plant ingredient or plant extract of *Sesamum*, and at least one pharmaceutically or cosmetically acceptable vehicle. Anti-oxidant responsive elements (AREs) mediate the transcriptional induction of a battery of genes which comprise much of this chemoprotective response system.

In addition to improving the aesthetic or cosmetic appearance of skin, the topical compositions of the present invention may be topically applied to enhance the general health, vitality and appearance of the skin. For example, the present composition may be applied to skin to improve microcirculation, communication among skin cells, replenishment of essential nutrients or skin constituents, or to improve the metabolism, proliferation, multiplication, turnover and/or exfoliation of skin cells.

Exfoliation may be carried out with or without the use of alpha- or beta hydroxy acids or other exfoliants, or combinations thereof by topical application to skin. When using exfoliating agents in the compositions of the present invention, sufficient anti-irritant or anti-inflammatory agents are included to neutralize the potential irritation associated with exfoliating agents in the absence of such neutralizing agents.

In certain embodiments, the compositions described herein may be used for various cosmetic and/or pharmaceutical applications including skin whitening and lightening.

Certain embodiments relate to a method of whitening skin that includes topically applying to the skin any composition described above and any combinations thereof.

The following are non-limiting examples of the present invention. Unless indicated otherwise, all proportions and percentages are by weight.

EXAMPLES

The following are examples of formulations and methods according to the present invention.

Example 1

Quinone Reductase Assay

This method was developed for screening plant extracts in order to identify inducers of quinone reductase, an enzyme that is activated by NRF2.

This assay provides a direct measurement of quinone reductase activity in cultured cells in order to identify inducers of antioxidant response pathway. Hepa 1c1c7 murine hepatoma cells were plated in 96-well microtiter plates, grown for 24 hours then exposed to inducing agents for another 48 hours. Cells were then lysed and quinone reductase activity was conducted.

Quinone reductase catalyzed the reduction of menadione to menadiol by NADPH, and MTT was reduced by menadiol resulting in the formation of a blue color which was measured on a microtiter plate reader at 610 nm.

The reagents and solutions included the following:
Deionized water, MiliQ grade or equivalent
50 mM Potassium phosphate (Fisher Scientific #SB 108-20) or equivalent.
Acetonitrile (Fisher# A998-4) or equivalent
Thioglucosidase from *Sinapis alba* (Myrosinase) (Sigma # T-4528 or equivalent)
EDTA Disodium Salt (Fisher # AC40997 or equivalent)
Dimethyl Sulfoxide (DMSO), HPLC grade or equivalent
Digitonin (Sigma # D-141 or equivalent)
Tris Base (Fisher # BP154-1 or equivalent)
Bovine Serum Albumin (Sigma # A3294 or equivalent)
Tween-20 (Aldrich #27,434-8 or equivalent)
Flavin Adenine Dinucleotide (FAD) (Sigma # F-6625 or equivalent)
Glucose-6-Phosphate (Sigma # G-7250 or equivalent)
NADP (Sigma # N-0505 or equivalent)
Glucose-6-Phosphate Dehydrogenase (Sigma # G7877 or equivalent)
MTT (Sigma # M21-28 or equivalent)
Medadione (Sigma# M-9429 or equivalent)
Dicoumarol (Sigma# M-1390 or equivalent)
DL-Sulforaphane (Sigma # S4441, or equivalent)
Pierce BCA Protein Assay Kit (Thermo Scientific#23225, or equivalent)

Cell Lines and culture medium included Murine hepatoma cells (Hepa 1c1c7), ATCC# CRL-2026; α-Minimum Essential Medium (Gibco#32561-037 or equivalent); Penicillin/Streptomycin (Sigma # P7539 or equivalent); Amphotericin B (Cellgro#30-003CF) or equivalent; and Charcoal Stripped Fetal Bovine Serum (FBS), (Fisher # NC9581766, or equivalent).

Lysis Buffer was prepared by combining 0.08% Digitonin in 2 mM EDTA, pH7.8. Stop Solution, 0.3 mM dicoumarol was prepared by dissolving 2.5 mg Dicoumarol in 250 uL 0.1 N NaOH and bringing to 25 mL in 5 mM Potassium Phosphate Buffer.

Cell culture plates were prepared for treatment with appropriate ingredients. About 20,000 c/mL cells were plated in clear cell culture treated 96 well plate and incubated overnight at 37 C, 5% $CO_2$.

Sample (100 mg/mL extract) was prepared by weighing 100 mg of plant material into a 1 mL centrifuge tube. 1 mL 70% DMSO was added into the tube, the tube was vortexed to mix and sonicated for 60 min.

Working solutions were prepared by diluting each sample in growth medium containing 3.5% DMSO to the following concentrations: 100 µg/mL, 50 µg/mL, 25 µg/mL, 12.5 µg/mL, 6.25 µg/mL, 3.125 µg/mL and 0 µg/mL, in a deep well dilution plate.

Controls were prepared by as follows.

Stock Solution was prepared by diluting DL-Sulforaphane to 100 mM in DMSO, freezing in PCR tubes at 50 µL/tube, and storing these stock dilutions at −20 C for up to 6 months.

Primary Dilution was 50 µM in growth medium.

Working solutions were prepared by dilute each sample in growth medium to the following concentrations: 5 uM, 4 uM, 1.35 uM, 0.450 uM, 0.150 uM and 0 uM in a deep well dilution plate.

The treatment procedure included adding 200 µl of each sample or control to the appropriate wells of the assay plate (FIG. 4) and incubating for 48 hours at 37° C., 5% $CO_2$.

To lyse cells, a lysis buffer was prepared by adding 0.5% Digitonin, mixing well and aspirating the treatment medium from all wells. Next, 50 µL Lysis buffer was added to all wells and wells were incubated for 20 min at room temperature.

Reagent preparation included:
0.5M Tris-HCl
1.5% Tween 20
150 mM Glucose-6-phosphante (120 mg+2 mL $H_2O$)
7.5 mM FAD (12.4 mg+2 mL $H_2O$)
50 mM NADP (76.5 mg+2 mL $H_2O$)
1000 u/mL Glucose-6-phosphate dehydrogenase (2KU+2 mL $H_2O$)
50 mM Menadione (17.2 mg+2 mL $H_2O$)
Reaction mix included the following:
2.5 mL 0.5M Tris-HCl
333 µL 1.5% Tween 20
333 µL 150 mM Glucose-6-Phosphate
33.3 µL 7.5 mM FAD
30 µL 50 mM NADP
100 µL 1000 U/mL Glucose-6-phosphate dehydrogenase
33.3 g Bovine Serum Albumin
15 mg MTT
46.74 mL Mili Q water
Just before adding to plate, 50 mM Menadione was added.

Stop reagent included:

2.5 mg Dicoumarol+250 uL 1N NaOH+250 uL $H_2O$. Vortex to mix.

2.5 mL 50 mM Phosphate Buffer+22 mL H2O+125 uL HCl (pH 7.4)

Next the assay plate was brought to room temperature on plate shaker. 200 uL of reaction mix was added to all wells and the wells were incubated at room temperature for 5 minutes. 50 µL stop solution was added to all wells.

The absorbance was read from bottom on M5 plate reader at 610 nm

Next the linear relationship between the absorbance of 0% (untreated) and 100% (1 nM) control was calculated. The % control of each sample concentration based on the 100% to 0% linear regression was determined. EC50 based on regression analysis of titrated samples was also determined. Sample results were reported out as the µg/mL EC50, based on % Control.

References:

Prochaska, H. J.; Santamaria, A. B. (1988) *Anal. Biochem.* 169:328-336.

Fahey et al. (2004) *Meth. Enzymol.* 382:243-258.

As demonstrated in FIG. 4, Quinone Reductase activity increased in dose dependent manner and is stimulated via ARE signaling pathway, which confirms strong anti-oxidant activity of kachnar.

Example 2

Kachnar Testing on Anti-Carbonylation Activity

The purpose of this experiment was to test Kachnar on anti-carbonylation assay using Hep G2 [HEPG2] (ATCC#HB-8065) cell line. The carbonylation process is related to protein degeneration and is similar to oxidation and glycation.

The following materials were used:

MEM (GIBCO #16600-082)

Fetal Bovine Serum (GIBCO #10099-141)

DPBS (Biosera #LM-52041)

Trypsin-EDTA (GIBCO #25200-072)

Cell culture Plates, 96 well (Corning #3599)

V-Bottom Plate, 96 well (Greiner #651101)

Round-Bottom Plates, 96 well (Corning #3365)

UV Multiwell plates, 96 well (Corning #3635)

DMSO (SIGMA #D2650)

OxiSelect™ Protein Carbonyl ELISA Kit (Cell Biology #STA-310)

On Day 1 of the procedure, Hep G2 [HEPG2] cells were plated on 96-well cell culture plates. To do so, disk was trypsinized and the cell density was determined. The cell slurry was diluted to the required volume at a density of 625,000 cells/ml. 160 ul/well of the cell slurry was dispensed onto assay plates. (100,000 cells per well). The assay plates were incubated overnight at 37 degrees C., 5% $CO_2$ under humidified conditions.

On Day 2, the cells were treated with Kachnar and Hydroquinone or Vitamin C as a reference.

200× compounds were prepared in 100% DMSO. Transfer 5 ul 200× compound was transferred to 95 ul completed medium (MEM with 10% FBS), and mixed 5 times.

| Dilution System | |
|---|---|
| ref/cpds (200×) | 5 µl/well |
| medium | 95 µl/well |
| Total (10×) | 100 µl/well |

20 ul 10× compound solution was transferred onto assay plates. The assay plates were incubated at 37 degrees C., 5% $CO_2$ under humidified conditions.

Day 3 included treatment with $H_2O_2$. 30 mM $H_2O_2$ solution was prepared and 20 ul/well of $H_2O_2$ solution was dispensed onto assay plates ($H_2O_2$ final conc. 3 mM). The assay plates were incubated for 4 hr at 37 degrees C., 5% $CO_2$ under humidified conditions.

| Reaction System | |
|---|---|
| ref/cpds (10×) | 20 µl/well |
| $H_2O_2$ (10×) | 20 µl/well |
| medium | 160 µl/well |
| Total | 200 µl/well |

Following the incubation, the cell culture medium was discarded and cells once washed once with PBS. 60 ul PBS was added onto assay plate, frozen at −80° C.

Day 4 included sample treatment and Elisa plate preparation.

Frozen samples were recovered 3 times. The lysed samples were transferred to V-bottom plate, centrifuged at 3000 rpm for 10 minutes at 4° C. The liquid supernatant was then transferred to compound plate. 5 ul of each cell lysis was obtained and the protein concentration was tested. The protein concentration was adjusted to 5 µg/ml with PBS and reduced BSA (total protein conc. 10 µg/ml), and mixed 5 times. 100 uL of the 5 ug/ml samples was then transferred onto the 96-well Protein Binding Plate, and incubated in 4° C. overnight.

To perform ELISA assay on Day 5, the wells were washed 3 times with 250 µL PBS per well and excess wash solution removed. 100 µL of the 0.04 mg/ml DNPH Working Solution was added and the plates were incubated for 45 minutes at room temperature in the dark. The plates were then washed 5 times with 250 µL of PBS/Ethanol (1:1, v/v) with incubation on an orbital shaker for 5 minutes. Next, the plates were washed 2 times with 250 µL of PBS. 200 µL of Blocking Solution was added per well and the plates were incubated for 2 hours at room temperature on an orbital shaker, and then washed 3 times with 250 µL of 1× Wash Buffer with thorough aspiration between each wash. 100 µL anti-DNP antibody was added and the plates were incubated for 1 hour at room temperature on an orbital shaker. Next, the strip wells were washed 3 times (1× wash buffer), 100 µL of the diluted HRP conjugated secondary antibody was added to all wells and plates were incubated for 1 hour at room temperature on an orbital shaker. The strip wells were then washed 5 times (1× wash buffer). The Substrate Solution was warmed to room temperature and 100 µL of Substrate Solution was added to each well, 5~20 min. The enzyme reaction was stopped by adding 100 µL of Stop Solution to each well. The absorbance of each well was read on a plate reader using 450 nm as the primary wave length, using the fully reduced BSA standard as absorbance blank.

Figure 5:
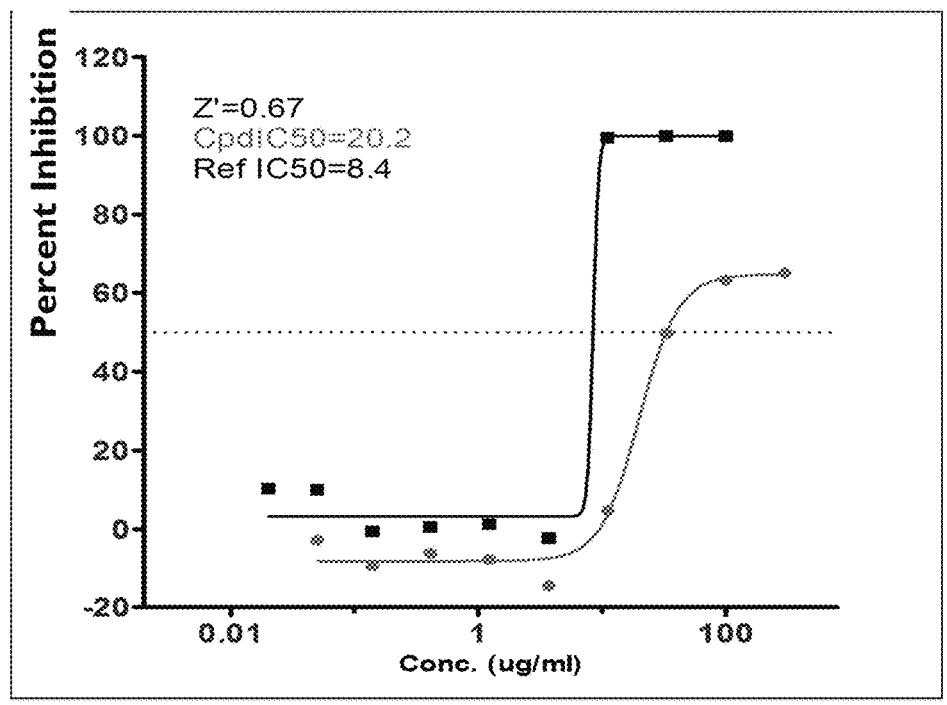
FIG. 5 shows a graph showing cell toxicity-CTG of Kachnar as compared to Hydroquinone in HepG2 cells.

Data Process included:
Signal=Sample 450 nm Signal−10 ug/ml Reduced BSA Signal
Protein Carbonyl Conc. (PCC)=(Signal−Y intercept)/Slope
% Inh=(Max PCC−Sample PCC)/(Max PCC−Min PCC)×100
   Max PCC was obtained from the cells treated with $H_2O_2$
   Min PCC was obtained from none treated cells
IC50 was calculated using GraphPad Prism V5.0 software The toxicity results are summarized in the following Table and shown in FIG. 5 for Kachnar as compared to Hydroquinone.

| Kachnar | | Hydroquinone | |
|---|---|---|---|
| BOTTOM | −8.110 | BOTTOM | 3.204 |
| TOP | 64.670 | TOP | 99.920 |
| LOGIC50 | 1.304 | LOGIC50 | 0.927 |
| HILLSLOPE | 2.748 | HILLSLOPE | 20.050 |
| IC50 | 20.160 | IC50 | 8.444 |

The carbonylation inhibition results are summarized in the following Table and shown in FIG. 6 for Kachnar as compared to Vitamin C.

| Kachnar | (%) | Vit. C | (%) |
|---|---|---|---|
| 300 ug/ml | 81.9 | 300 ug/ml | 49.1 |
|  | 54.5 |  | 76.2 |
| 150 ug/ml | 48.2 | 100 ug/ml | 46.1 |
|  |  |  | 64.6 |
| 37.5 ug/ml | 31.2 | 33 ug/ml | 33.5 |
|  | 26.5 |  | 28.6 |
| 0 ug/ml | −5.0 | 0 ug/ml | −2.3 |
|  | 11.0 |  | −3.8 |

In conclusion, the data demonstrate that Kachnar has an equal or higher activity of protein carbonylation inhibition compared with Vitamin C.

Example 3

NRF2 Induction by Sesamin and Kachnar

To determine whether Kachnar and/or Sesamin induced NRF2, which is a master regulator of total antioxidant, stably transfected HepG2 cells expressing the ARE luciferase reporter were plated ($1\times10^4$ cells/well) in white-walled, clear-bottom, 96-well plates and incubated for 48 h in a 37° C., 5% $CO_2$ incubator. The cells were then treated with Sesamin and Kachnar compounds at specified concentrations for an additional 48 h. Sulforaphane (10 μM), a known activator of NRF2, was used as a positive control. Luciferase activity was quantified using a luciferase assay kit (Biotium, Inc., Hayward, Calif.) according to manufacturer's instructions. Briefly, cells were rinsed with PBS (100 μL), and then lysed with a lysis buffer (20 μL) for 15 min at room temperature. D-luciferin (100 μL) was added and light emission read immediately on a SpectraMax M5 spectrophotometer (Molecular Devices, Sunnyvale, Calif.). Data were plotted as relative light units (RLUs) against test compounds using GraphPad Prism software (San Diego, Calif.).

To determine protein expression, Western blot analysis was conducted as follows: HepG2 cells were treated with different concentrations of Sesamin and Kachnar and incubated overnight. Next day cells were washed with ice cold phosphate buffered saline once and then the cells were collected using a cell scraper into a microcentrifuge tube. The cells were lysed using RIPA buffer for 30' in ice. After lysis the tubes were centrifuged and the cell lysate transferred to a new tube. Protein was estimated and a total of 50 μg of total protein per sample was loaded in polyacrylamide gel and electrophoresed. The electrophoresed protein were next transferred to a membrane via electric current. The electro blotted membrane was blocked with blocking buffer for 1 hr at room temperature. The membrane was hybridized with NRF2 antibody over night at 8° C. and then washed 3 times with washing buffer. Then secondary antibody was added to bind to the NRF2 antibody for 1 hr and excess of secondary antibody was washed. The NRF2 protein was visualized after the addition of developing buffer the membrane and photographed using the Bio-Rad gel documentation system.

As shown in FIG. 7, Kachnar (12.5 μg/ml and 25 μg/ml) and Sesamin (25 μg/ml and 50 μg/ml), individually, induced NRF2, which is a master regulator of total anti-oxidant activity, as compared to a control.

Example 4

Hemeoxygenase Gene Expression

Hepa1c1c7 cells were plated ($2\times10^5$ cells/well) in 6-well culture plates, incubated overnight, and then, incubated for 24 h with select concentrations of magnolia bark extract. The cells were rinsed with PBS and total RNA purified using the RNeasy Plus mini kit, according to manufacturer's instructions. Total RNA was quantified using the A260/A280 ratio, diluted to 1 μg per reaction, and reverse transcribed using the iScript cDNA synthesis kit.

Real-time qPCR reactions were performed using SsoFast EvaGreen qPCR mix on a CFX96 Real-Time Thermocycler (Bio-Rad). The reaction conditions were as follows: 95° C. for 30 sec; 40 cycles of 58° C. for 5 sec; and 95° C. for 5 sec. Fluorescent detection was measured following completion of each cycle. Cycle times of the NRF2-dependent genes were normalized to the housekeeping gene by 2(−Delta Delta C(T)) method (Livak and Schmittgen, 2001), GAPDH, prior to comparisons with control samples.

Figure 8:
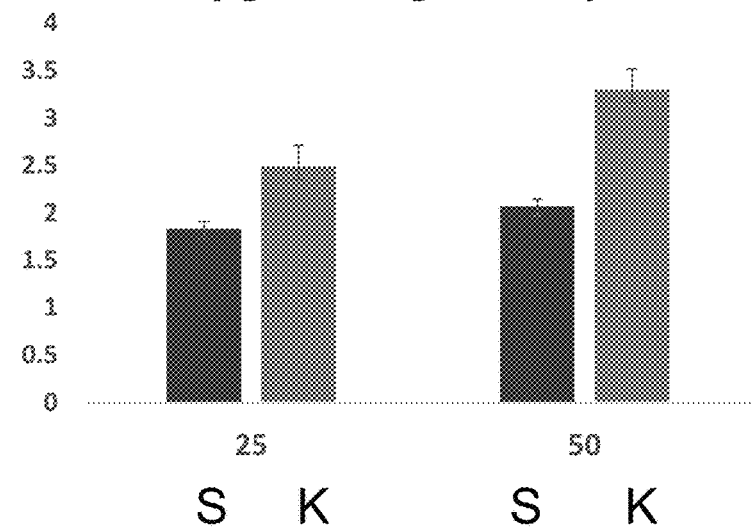
FIG. 8 depict s graph showing results from qPCR for Hemeoxygenase gene expression for Sesamin and Kachnar.

As shown in FIG. 8, both, Sesamin and Kachnar, at 25 and 50 μg/ml induce hemeoxygenase gene expression, as determined by qPCR. The expression of hemeoxygenase gene was greater due to the treatment with Kachnar as compared to Sesamin at the two concentrations studied.

Example 5

Characterization of Phytochemicals in Hydrolyzed *Bauhinia variegata/purpurea* L. (Kachnar) Bark Extract A water extract from the bark of *Bauhinia variegate/purpurea* L (common name: Kachnar, origin from India), was obtained as a dried, milled powder from Verdure Sciences, Noblesville, Ind. USA.

Procedure for Acid Hydrolysis of Powdered Extract:
Reagents: Methanol (MeOH), HPLC grade; concentrated hydrochloric acid (HCl), ACS grade About 150 mg of powered extract was weighed, to the nearest 0.1 mg, into a 25 mm×150 mm screw cap Pyrex tube. 10 mL of 85/15 MeOH/HCl was pipetted and the cap was tightly secured. The tube was them vortexed for at least 2 minutes and then a mini-stir bar was placed in the Pyrex tube. The Pyrex tube was placed in a heat block equipped with a magnetic stirrer and stirred at high speed. The temperature was maintained at 90° C. to 95° C. for one hour. Next, the Pyrex tube was removed from the heating block and cooled to room temperature. Next, 20 mL MeOH was pipetted into the Pyrex tube, the tube was re-caped, and mixed well. An aliquot was filtered through a 0.45 um HVLP syringe filter into an HPLC vial.

Procedure for High Performance Liquid Chromatography (HPLC) Analysis:

Instrumentation: HPLC system equipped with an autosampler, column heater, UV detector and data system.

Reagents: water, HPLC grade; acetonitrile, HPLC grade; phosphoric acid (H3PO4), ACS grade.

Solvents: solvent A—0.2% H3PO4 in Water; solvent B—acetonitrile

HPLC Analytical Column: Phenomenex Kinetex 2.6 µm C 18 100 Å, 100×4.6 mm.

Gradient Mobile Phase Program:

| Time, min | Solvent A, % | Solvent B, % |
|---|---|---|
| 0 | 90 | 10 |
| 6 | 80 | 20 |
| 8 | 50 | 50 |
| 9 | 50 | 50 |
| 10 | 90 | 10 |

Figure 9:
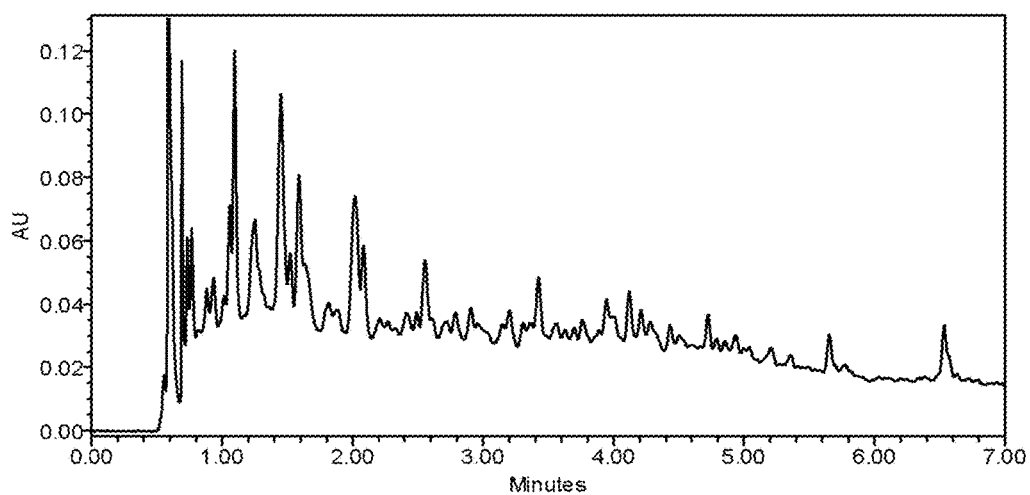
FIG. 9 shows the chromatogram of unhydrolyzed *Bauhinia variegate/purpurea* L bark extract.

Flow Rate: 0.7 mL/min, Column Temperature: 40° C., Injection Volume: 10 µL, Detection Wavelength: 210 nm, Integration: Peak area, Run Time: 12 minutes FIG. 9 shows the chromatogram of unhydrolyzed *Bauhinia variegate/purpurea* bark extract.

Figure 10:
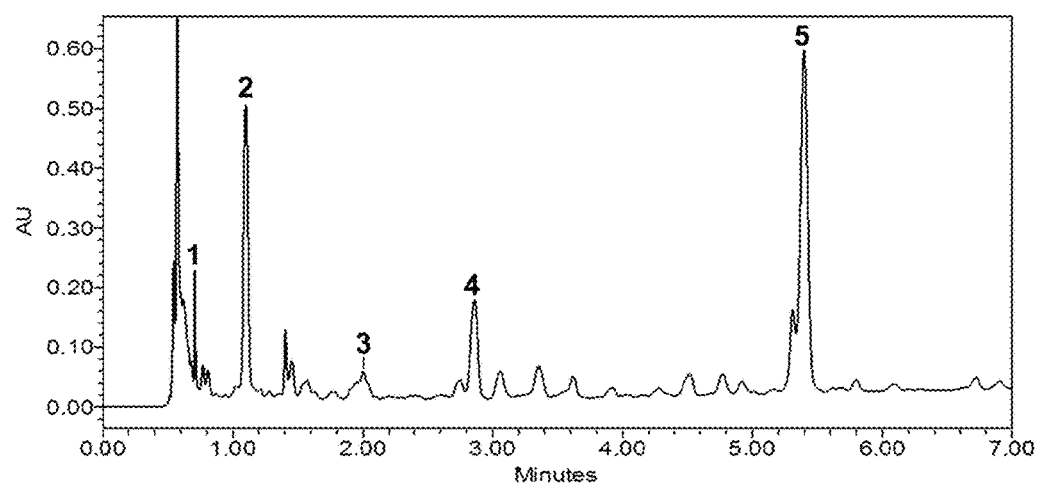
FIG. 10 shows the chromatogram of acid hydrolyzed *Bauhinia variegate/purpurea* L bark extract.

FIG. 10 shows the chromatogram of acid hydrolyzed *Bauhinia variegate/purpurea* bark extract. Peak are identified based on retention time, UV spectrum, and mass spectral analysis: 1, quinic acid; 2, protocatechuic acid; 3, caffeic acid; 4, vanillic acid; and 5, ferulic acid.

It is therefore intended that the foregoing detailed description be regarded as illustrative rather than limiting, and that it be understood that it is the following claims, including all equivalents, that are intended to define the spirit and scope of this invention.

The invention claimed is:

1. A method of stimulating or increasing Quinone Reductase activity in a skin cell in a subject in need thereof comprising applying to the skin a composition in a cosmetically effective amount sufficient to stimulate or increase Quinone Reductase activity in the skin, wherein the composition comprises:

a. a plant ingredient or plant extract from *Bauhinia*, individually or in combination with an amount of a plant ingredient or plant extract from *Sesamum*, the amounts, individually or in combination capable of stimulating or increasing Quinone Reductase activity; and b. at least one pharmaceutically or cosmetically acceptable vehicle.

2. The method of claim 1, wherein the composition further comprises at least one DNA repair enzyme.

3. The method of claim 2, where the at least one DNA repair enzyme is a pyrimidine glycosylate/abasic lyase.

4. The method of claim 2, wherein the at least one DNA repair enzyme is selected from the group consisting of a bacteriophage T4 pyrimidine dimer-specific endonuclease, a *Micrococcus luteus* N-glycosylase/AP lyase, a *Saccharomyces cerevisiae* N-glycosylase/apurinic-apyrimidinic lyase, a *Schizosaccharomyces pombe* UV damage endonuclease (UVDE), a Chlorella virus isolate PBCV-I pyrimidine dimer-specific glycosylase, an *Anacystis nidulans* photolyase, and combinations thereof.

5. The method of claim 1, wherein the composition is in a product form selected from the group consisting of an aerosol, a cream, a emulsion, a solid, a liquid, a dispersion, a foam, a gel, a lotion, a mousse, an ointment, a powder, a patch, a pomade, a solution, a pump a spray, a stick, a towelette, and combinations thereof.

6. The method of claim 1, wherein the at least one pharmaceutically or cosmetically acceptable vehicle comprises one or more ingredients selected from the group consisting of water, a glycerin, a C1 -C4 alcohol, a fatty alcohol, a fatty ether, a fatty ester, a polyol, a glycol, a vegetable oil, a mineral oil, a liposome, a laminar lipid material, a silicone oil, and combinations thereof.

7. The method of claim 1, wherein the composition has a substantially neutral pH.

8. The method of claim 1, wherein the composition further comprises a skin whitening agent selected from the group consisting of tyrosinase inhibitors, free radical scavengers, and mixtures thereof.

9. The method of claim 1, wherein the amount of *Bauhinia*, individually or in combination with a plant ingredient or plant extract from *Sesamum*, ranges from about 0.0001% to 5% by weight of the total composition.

10. The method of claim 1, wherein the amount of *Bauhinia*, individually or in combination with a plant ingredient or plant extract from *Sesamum*, ranges from about 0.001% to about 0.5% by weight of the total composition.

11. The method of claim 1, wherein the amount of *Bauhinia*, individually or in combination with a plant ingredient or plant extract from *Sesamum*, ranges from about 0.01% to about 0.1% by weight of the total composition.

* * * * *